(12) United States Patent
Kekare et al.

(10) Patent No.: US 7,769,225 B2
(45) Date of Patent: Aug. 3, 2010

(54) METHODS AND SYSTEMS FOR DETECTING DEFECTS IN A RETICLE DESIGN PATTERN

(75) Inventors: Sagar A. Kekare, Plano, TX (US); Ingrid B. Peterson, Menlo Park, CA (US); Moshe E. Preil, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 608 days.

(21) Appl. No.: 11/314,813

(22) Filed: Dec. 20, 2005
(Under 37 CFR 1.47)

(65) Prior Publication Data
US 2007/0035728 A1    Feb. 15, 2007

Related U.S. Application Data

(60) Provisional application No. 60/704,806, filed on Aug. 2, 2005.

(51) Int. Cl.
*G06K 9/00* (2006.01)
*G01N 21/00* (2006.01)
*G01B 5/28* (2006.01)

(52) U.S. Cl. .......... 382/145; 382/144; 382/146; 382/147; 382/148; 382/149; 356/237.4; 356/237.5; 356/237.6; 702/35

(58) Field of Classification Search .......... 382/141
See application file for complete search history.

(56) References Cited

U.S. PATENT DOCUMENTS

| | | | |
|---|---|---|---|
| 3,495,269 A | 2/1970 | Mutschler et al. | |
| 3,496,352 A | 2/1970 | Jugle | |
| 3,909,602 A | 9/1975 | Micka | |
| 4,015,203 A | 3/1977 | Verkuil | |
| 4,247,203 A | 1/1981 | Levy et al. | |
| 4,347,001 A * | 8/1982 | Levy et al. | 356/398 |
| 4,378,159 A | 3/1983 | Galbraith | |

(Continued)

FOREIGN PATENT DOCUMENTS

EP    0032197    4/1984

(Continued)

OTHER PUBLICATIONS

U.S. Appl. No. 11/960,157, filed Dec. 2007, Kulkarni et al.

(Continued)

*Primary Examiner*—Vikkram Bali
*Assistant Examiner*—Michelle Entezari
(74) *Attorney, Agent, or Firm*—Ann Marie Mewherter

(57) ABSTRACT

Computer-implemented methods and systems for detecting defects in a reticle design pattern are provided. One computer-implemented method includes acquiring images of a field in the reticle design pattern. The images illustrate how the field will be printed on a wafer at different values of one or more parameters of a wafer printing process. The field includes a first die and a second die. The method also includes detecting defects in the field based on a comparison of two or more of the images corresponding to two or more of the different values. In addition, the method includes determining if individual defects located in the first die have substantially the same within die position as individual defects located in the second die.

19 Claims, 16 Drawing Sheets

U.S. PATENT DOCUMENTS

| | | | |
|---|---|---|---|
| 4,448,532 A | 5/1984 | Joseph et al. | |
| 4,532,650 A | 7/1985 | Wihl et al. | |
| 4,555,798 A | 11/1985 | Broadbent, Jr. et al. | |
| 4,578,810 A | 3/1986 | MacFarlane et al. | |
| 4,579,455 A | 4/1986 | Levy et al. | |
| 4,595,289 A | 6/1986 | Feldman et al. | |
| 4,599,558 A | 7/1986 | Castellano et al. | |
| 4,633,504 A | 12/1986 | Wihl | |
| 4,641,353 A | 2/1987 | Kobayashi | |
| 4,641,967 A | 2/1987 | Pecen | |
| 4,734,721 A | 3/1988 | Boyer et al. | |
| 4,758,094 A | 7/1988 | Wihl | |
| 4,766,324 A | 8/1988 | Saadat et al. | |
| 4,799,175 A * | 1/1989 | Sano et al. | 382/151 |
| 4,805,123 A | 2/1989 | Specht et al. | |
| 4,812,756 A | 3/1989 | Curtis et al. | |
| 4,814,829 A * | 3/1989 | Kosugi et al. | 355/43 |
| 4,817,123 A | 3/1989 | Sones et al. | |
| 4,845,558 A | 7/1989 | Tsai et al. | |
| 4,877,326 A | 10/1989 | Chadwick et al. | |
| 4,926,489 A | 5/1990 | Danielson et al. | |
| 4,928,313 A | 5/1990 | Leonard et al. | |
| 5,046,109 A | 9/1991 | Fujimori et al. | |
| 5,189,481 A | 2/1993 | Jann et al. | |
| 5,240,866 A * | 8/1993 | Friedman et al. | 702/35 |
| 5,444,480 A | 8/1995 | Sumita | |
| 5,453,844 A | 9/1995 | George et al. | |
| 6,459,520 B1 | 10/1995 | Sasaki | |
| 5,481,624 A | 1/1996 | Kamon | |
| 5,485,091 A | 1/1996 | Verkuil | |
| 5,528,153 A | 6/1996 | Taylor et al. | |
| 5,544,256 A * | 8/1996 | Brecher et al. | 382/149 |
| 5,563,702 A | 10/1996 | Emery et al. | |
| 5,572,598 A | 11/1996 | Wihl et al. | |
| 5,594,247 A | 1/1997 | Verkuil et al. | |
| 5,608,538 A | 3/1997 | Edgar et al. | |
| 5,619,548 A | 4/1997 | Koppel | |
| 5,621,519 A | 4/1997 | Frost et al. | |
| 5,644,223 A | 7/1997 | Verkuil | |
| 5,650,731 A | 7/1997 | Fung | |
| 5,661,408 A | 8/1997 | Kamieniecki et al. | |
| 5,689,614 A | 11/1997 | Gronet et al. | |
| 5,694,478 A * | 12/1997 | Braier et al. | 382/133 |
| 5,696,835 A | 12/1997 | Hennessey et al. | |
| 5,703,969 A | 12/1997 | Hennessey et al. | |
| 5,737,072 A | 4/1998 | Emery et al. | |
| 5,742,658 A | 4/1998 | Tiffin et al. | |
| 5,754,678 A | 5/1998 | Hawthorne et al. | |
| 5,767,691 A | 6/1998 | Verkuil | |
| 5,767,693 A | 6/1998 | Verkuil | |
| 5,771,317 A | 6/1998 | Edgar | |
| 5,773,989 A | 6/1998 | Edelman et al. | |
| 5,774,179 A | 6/1998 | Chevrette et al. | |
| 5,795,685 A | 8/1998 | Liebmann et al. | |
| 5,814,728 A * | 9/1998 | Okawa et al. | 73/587 |
| 5,834,941 A | 11/1998 | Verkuil | |
| 5,852,232 A | 12/1998 | Samsavar et al. | |
| 5,866,806 A | 2/1999 | Samsavar et al. | |
| 5,874,733 A * | 2/1999 | Silver et al. | 250/231.18 |
| 5,884,242 A | 3/1999 | Meier et al. | |
| 5,889,593 A | 3/1999 | Bareket | |
| 5,932,377 A | 8/1999 | Ferguson et al. | |
| 5,940,458 A | 8/1999 | Suk | |
| 5,948,972 A | 9/1999 | Samsavar et al. | |
| 5,955,661 A | 9/1999 | Samsavar et al. | |
| 5,965,306 A | 10/1999 | Mansfield et al. | |
| 5,980,187 A | 11/1999 | Verhovsky | |
| 5,986,263 A | 11/1999 | Hiroi et al. | |
| 5,991,699 A * | 11/1999 | Kulkarni et al. | 702/83 |
| 6,011,404 A | 1/2000 | Ma et al. | |
| 6,014,461 A | 1/2000 | Hennessey et al. | |
| 6,052,478 A | 4/2000 | Wihl et al. | |
| 6,060,709 A | 5/2000 | Verkuil et al. | |
| 6,072,320 A | 6/2000 | Verkuil | |
| 6,076,465 A | 6/2000 | Vacca et al. | |
| 6,078,738 A | 6/2000 | Garza et al. | |
| 6,091,257 A | 7/2000 | Verkuil et al. | |
| 6,091,846 A | 7/2000 | Lin et al. | |
| 6,097,196 A | 8/2000 | Verkuil et al. | |
| 6,097,887 A * | 8/2000 | Hardikar et al. | 717/105 |
| 6,104,206 A | 8/2000 | Verkuil | |
| 6,104,835 A | 8/2000 | Han | |
| 6,121,783 A | 9/2000 | Horner et al. | |
| 6,122,017 A | 9/2000 | Taubman | |
| 6,122,046 A | 9/2000 | Almogy | |
| 6,137,570 A | 10/2000 | Chuang et al. | |
| 6,141,038 A | 10/2000 | Young et al. | |
| 6,146,627 A | 11/2000 | Muller | |
| 6,171,737 B1 | 1/2001 | Phan et al. | |
| 6,175,645 B1 | 1/2001 | Elyasaf et al. | |
| 6,184,929 B1 | 2/2001 | Noda et al. | |
| 6,184,976 B1 | 2/2001 | Park et al. | |
| 6,191,605 B1 | 2/2001 | Miller et al. | |
| 6,201,999 B1 | 3/2001 | Jevtic | |
| 6,202,029 B1 | 3/2001 | Verkuil et al. | |
| 6,205,239 B1 | 3/2001 | Lin et al. | |
| 6,224,638 B1 | 5/2001 | Jevtic et al. | |
| 6,233,719 B1 * | 5/2001 | Hardikar et al. | 716/1 |
| 6,248,485 B1 | 6/2001 | Cuthbert | |
| 6,248,486 B1 | 6/2001 | Dirksen et al. | |
| 6,259,960 B1 | 7/2001 | Inokuchi | |
| 6,266,437 B1 | 7/2001 | Eichel et al. | |
| 6,267,005 B1 | 7/2001 | Samsavar et al. | |
| 6,268,093 B1 | 7/2001 | Kenan et al. | |
| 6,272,236 B1 | 8/2001 | Pierrat et al. | |
| 6,282,309 B1 | 8/2001 | Emery | |
| 6,292,582 B1 * | 9/2001 | Lin et al. | 382/149 |
| 6,344,640 B1 | 2/2002 | Rhoads | |
| 6,363,166 B1 | 3/2002 | Wihl et al. | |
| 6,373,975 B1 | 4/2002 | Bula et al. | |
| 6,415,421 B2 | 7/2002 | Anderson et al. | |
| 6,445,199 B1 | 9/2002 | Satya et al. | |
| 6,451,690 B1 | 9/2002 | Matsumoto | |
| 6,466,314 B1 | 10/2002 | Lehman | |
| 6,466,315 B1 | 10/2002 | Karpol et al. | |
| 6,470,489 B1 | 10/2002 | Chang et al. | |
| 6,483,938 B1 | 11/2002 | Hennessey et al. | |
| 6,513,151 B1 | 1/2003 | Erhardt et al. | |
| 6,526,164 B1 | 2/2003 | Mansfield et al. | |
| 6,529,621 B1 | 3/2003 | Glasser et al. | |
| 6,535,628 B2 * | 3/2003 | Smargiassi et al. | 382/149 |
| 6,569,691 B1 | 5/2003 | Jastrzebski et al. | |
| 6,581,193 B1 | 6/2003 | McGhee et al. | |
| 6,593,748 B1 | 7/2003 | Halliyal et al. | |
| 6,597,193 B2 | 7/2003 | Lagowski et al. | |
| 6,602,728 B1 | 8/2003 | Liebmann et al. | |
| 6,608,681 B2 * | 8/2003 | Tanaka et al. | 356/400 |
| 6,614,520 B1 | 9/2003 | Bareket et al. | |
| 6,631,511 B2 | 10/2003 | Haffner | |
| 6,636,301 B1 | 10/2003 | Kvamme et al. | |
| 6,642,066 B1 | 11/2003 | Halliyal et al. | |
| 6,658,640 B2 | 12/2003 | Weed | |
| 6,665,065 B1 | 12/2003 | Phan et al. | |
| 6,670,082 B2 | 12/2003 | Liu et al. | |
| 6,680,621 B2 | 1/2004 | Savtchouk et al. | |
| 6,691,052 B1 | 2/2004 | Maurer | |
| 6,701,004 B1 | 3/2004 | Shykind et al. | |
| 6,718,526 B1 | 4/2004 | Eldredge et al. | |
| 6,721,695 B1 | 4/2004 | Chen et al. | |
| 6,734,696 B2 | 5/2004 | Horner et al. | |
| 6,748,103 B2 | 6/2004 | Glasser | |
| 6,751,519 B1 | 6/2004 | Satya et al. | |
| 6,753,954 B2 | 6/2004 | Chen | |
| 6,757,645 B2 | 6/2004 | Chang | |

| | | |
|---|---|---|
| 6,775,818 B2 | 8/2004 | Taravade et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,782,525 B2* | 8/2004 | Garza et al. ............ 716/19 |
| 6,788,400 B2 | 9/2004 | Chen |
| 6,789,032 B2* | 9/2004 | Barbour et al. ............ 702/81 |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1* | 1/2005 | Irie ............ 355/67 |
| 6,859,746 B1 | 2/2005 | Stirton |
| 6,879,924 B2 | 4/2005 | Ye et al. |
| 6,882,745 B2 | 4/2005 | Brankner |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1* | 1/2006 | Martinent-Catalot et al. ..... 382/100 |
| 6,988,045 B2 | 1/2006 | Purdy |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2* | 9/2006 | Chang et al. ............ 716/19 |
| 7,111,277 B2 | 9/2006 | Ye et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski |
| 7,124,386 B2 | 10/2006 | Smith |
| 7,133,548 B2 | 11/2006 | Kenan et al. |
| 7,135,344 B2 | 11/2006 | Nehmadi |
| 7,136,143 B2 | 11/2006 | Smith |
| 7,152,215 B2 | 12/2006 | Smith |
| 7,171,334 B2 | 1/2007 | Gassner |
| 7,174,520 B2 | 2/2007 | White |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,379,175 B1 | 5/2008 | Stokowski et al. |
| 7,386,839 B1* | 6/2008 | Golender et al. ............ 717/131 |
| 7,418,124 B2 | 8/2008 | Peterson et al. |
| 7,424,145 B2 | 9/2008 | Horie et al. |
| 2001/0019625 A1 | 9/2001 | Kenan et al. |
| 2001/0022858 A1 | 9/2001 | Komiya et al. |
| 2001/0043735 A1* | 11/2001 | Smargiassi et al. .......... 382/149 |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1* | 3/2002 | Chang et al. ............ 703/13 |
| 2002/0035641 A1 | 3/2002 | Kurose |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0164065 A1 | 11/2002 | Cai et al. |
| 2002/0181756 A1 | 12/2002 | Shibuya et al. |
| 2002/0186878 A1* | 12/2002 | Hoon et al. ............ 382/149 |
| 2002/0192578 A1 | 12/2002 | Tanaka et al. |
| 2003/0014146 A1 | 1/2003 | Fujii |
| 2003/0022401 A1 | 1/2003 | Hamamatsu et al. |
| 2003/0033046 A1 | 2/2003 | Yoshitake et al. |
| 2003/0048458 A1 | 3/2003 | Mieher |
| 2003/0048939 A1 | 3/2003 | Lehman |
| 2003/0057971 A1 | 3/2003 | Nishiyama et al. |
| 2003/0086081 A1 | 5/2003 | Lehman |
| 2003/0098805 A1* | 5/2003 | Bizjak ............ 341/139 |
| 2003/0128870 A1 | 7/2003 | Pease et al. |
| 2003/0138138 A1* | 7/2003 | Vacca et al. ............ 382/145 |
| 2003/0138978 A1* | 7/2003 | Tanaka et al. ............ 438/5 |
| 2003/0169916 A1* | 9/2003 | Hayashi et al. ............ 382/145 |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0228714 A1 | 12/2003 | Smith |
| 2003/0229410 A1 | 12/2003 | Smith |
| 2003/0229412 A1 | 12/2003 | White |
| 2003/0229868 A1 | 12/2003 | White |
| 2003/0229875 A1 | 12/2003 | Smith |
| 2003/0229880 A1 | 12/2003 | White |
| 2003/0229881 A1 | 12/2003 | White |
| 2003/0237064 A1* | 12/2003 | White et al. ............ 716/5 |
| 2004/0030430 A1 | 2/2004 | Matsuoka |
| 2004/0032908 A1* | 2/2004 | Hagai et al. ............ 375/240.25 |
| 2004/0091142 A1* | 5/2004 | Peterson et al. ............ 382/144 |
| 2004/0098216 A1 | 5/2004 | Ye et al. |
| 2004/0107412 A1 | 6/2004 | Pack et al. |
| 2004/0119036 A1 | 6/2004 | Ye et al. |
| 2004/0133369 A1* | 7/2004 | Pack et al. ............ 702/59 |
| 2004/0174506 A1 | 9/2004 | Smith |
| 2004/0228515 A1* | 11/2004 | Okabe et al. ............ 382/145 |
| 2004/0243320 A1* | 12/2004 | Chang et al. ............ 702/30 |
| 2005/0004774 A1 | 1/2005 | Volk et al. |
| 2005/0008218 A1* | 1/2005 | O'Dell et al. ............ 382/145 |
| 2005/0010890 A1 | 1/2005 | Nehmadi et al. |
| 2005/0062962 A1* | 3/2005 | Fairley et al. ............ 356/237.2 |
| 2005/0117796 A1 | 6/2005 | Matoui et al. |
| 2005/0132306 A1 | 6/2005 | Smith |
| 2005/0166174 A1 | 7/2005 | Ye et al. |
| 2005/0190957 A1 | 9/2005 | Cai et al. |
| 2005/0198602 A1 | 9/2005 | Brankner |
| 2006/0000964 A1 | 1/2006 | Ye et al. |
| 2006/0048089 A1 | 3/2006 | Schwarzband |
| 2006/0051682 A1 | 3/2006 | Hess et al. |
| 2006/0062445 A1 | 3/2006 | Verma |
| 2006/0082763 A1* | 4/2006 | Teh et al. ............ 356/72 |
| 2006/0159333 A1 | 7/2006 | Ishikawa ............ 382/149 |
| 2006/0161452 A1 | 7/2006 | Hess |
| 2006/0193506 A1* | 8/2006 | Dorphan et al. ............ 382/145 |
| 2006/0193507 A1* | 8/2006 | Sali et al. ............ 382/145 |
| 2006/0236297 A1 | 10/2006 | Melvin et al. |
| 2006/0265145 A1* | 11/2006 | Huet et al. ............ 702/35 |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0292463 A1* | 12/2006 | Best et al. ............ 430/22 |
| 2007/0002322 A1* | 1/2007 | Borodovsky et al. ............ 356/394 |
| 2007/0019171 A1 | 1/2007 | Smith |
| 2007/0031745 A1 | 2/2007 | Ye et al. |
| 2007/0032896 A1 | 2/2007 | Ye et al. |
| 2007/0035712 A1 | 2/2007 | Gassner et al. |
| 2007/0052963 A1 | 3/2007 | Orbon |

| | | |
|---|---|---|
| 2008/0049994 A1* | 2/2008 | Rognin et al. ............... 382/128 |

FOREIGN PATENT DOCUMENTS

| | | |
|---|---|---|
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1480034 | 8/2006 |
| EP | 1696270 | 8/2006 |
| JP | 2002-071575 | 3/2002 |
| KR | 1020030055848 | 7/2003 |
| WO | WO 98/57358 | 12/1998 |
| WO | WO 99/22310 | 5/1999 |
| WO | WO 99/25004 | 5/1999 |
| WO | WO 99/38002 | 7/1999 |
| WO | WO 99/41434 | 8/1999 |
| WO | WO 99/59200 | 11/1999 |
| WO | WO 00/03234 | 1/2000 |
| WO | WO 00/36525 | 6/2000 |
| WO | WO 00/55799 | 9/2000 |
| WO | WO 00/68884 | 11/2000 |
| WO | WO 00/70332 | 11/2000 |
| WO | WO 01/09566 | 2/2001 |
| WO | WO 01/40145 | 6/2001 |
| WO | WO 03/104921 | 12/2003 |
| WO | WO 2004/027684 | 4/2004 |
| WO | WO 2006/063268 | 6/2006 |

OTHER PUBLICATIONS

U.S. Appl. No. 11/970,294, filed Jan. 2008, Park et al.
Lorusso et al. "Advanced DFM Applns. Using design-based metrology on CDSEM," SPIE vol. 6152, Mar. 27, 2006.
Svidenko et al. "Dynamic Defect-Limited Yield Prediction by Criticality Factor," ISSM Paper: YE-O-157, 2007.
U.S. Appl. No. 60/609,670, filed Sep. 14, 2004, Preil.
U.S. Appl. No. 60/772,418, filed Feb. 9, 2006, Kirk et al.
U.S. Appl. No. 11/673,150, filed Feb. 9, 2007, Kirk et al.
U.S. Appl. No. 10/778,752, filed Feb. 13, 2004, Mack.
U.S. Appl. No. 11/154,310, filed Jun. 16, 2005, Verma et al.
U.S. Appl. No. 11/561,735, filed Nov. 20, 2006, Kulkarni et al.
U.S. Appl. No. 11/561,659, filed Nov. 20, 2006, Zafar et al.
Volk et al., "Investigation of Smart Inspection of Critical Layer Reticles using Additional Designer Data to Determine Defect Significance," Proceedings of SPIE vol. 5256, 2003, pp. 489-499.
Mack, "Lithographic Simulation: A Review," Proceedings of SPIE vol. 4440, 2001, pp. 59-72.
Lo et al., "Identifying Process Window Marginalities of Reticle Designs for 0.15/0.13 μm Technologies," Proceedings of SPIE vol. 5130, 2003, pp. 829-837.
Dirksen et al., "Impact of high order aberrations on the performance of the aberration monitor," Proc. of SPIE vol. 4000, Mar. 2000, pp. 9-17.
Dirksen et al., "Novel aberration monitor for optical lithography," Proc. of SPIE vol. 3679, Jul. 1999, pp. 77-86.
U.S. Appl. No. 11/830,485, filed Jul. 2007, Kulkarni et al.
U.S. Appl. No. 11/950,961, filed Dec. 2007, Fouquet et al.
U.S. Appl. No. 12/102,343, filed Apr. 2008, Chen et al.
Svidenko et al. "Dynamic Defect-Limited Yield Prediction by Criticality Factor," ISSM Paper YE-O-157, 2007.
U.S. Appl. No. 60/418,994 entitled Methods and Systems for Reticle Inspection and Defect Review Using Aerial Imaging, filed Oct. 15, 2002.
U.S. Appl. No. 60/451,707 entitled Methods and Systems for Classifying and Analyzing Defects on Reticles, filed Mar. 4, 2003.
U.S. Appl. No. 60/738,290 entitled Methods and Systems for Utilizing Design Data in Combination With Inspection Data, filed Nov. 18, 2005.
U.S. Appl. No. 10/679,617 entitled Methods and Systems for Reticle Inspection and Defects Review Using Aerial Imaging, filed Oct. 6, 2003.
U.S. Appl. No. 10/793,599 entitled Methods and Systems for Classifying and Analyzing Defects on Reticles, filed Mar. 4, 2004.
U.S. Appl. No. 11/005,658 entitled Computer-Implemented Methods for Detecting and/or Sorting Defects in a Design Pattern of a Reticle, filed Dec. 7, 2004.
U.S. Appl. No. 11/048,630 entitled Computer-Implemented Methods for Detecting Defects in Reticle Design Data, filed Jan. 31, 2005.
U.S. Appl. No. 11/300,172 entitled Methods and Systems for Binning Defects Detected on a Specimen, filed Dec. 14, 2005.
U.S. Appl. No. 11/759,607, filed Jun. 7, 2007, Kulkarni et al.
U.S. Appl. No. 11/837,208, filed Aug. 2007, Park.
Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automoated Defect Severity Scoring," Proceedings of the SPIE, vol. 4409, Jan. 2001, pp. 467-478.
Comizzoli, "Uses of Corono Discharges in the Semiconfuctor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and produiction metrology of thin transistor gate oxide films," Materials Science in Semiconductor Processing 2, 1999, pp. 103-147.
Garcia et al., "New Die to Database Inspection Algorithm for Inspection of 90-nm Node Reticles," Proceedings of SPIE, vol. 5130, 2003, pp. 364-374.
Granik et al., "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
International Search Report and Written Opinion for PCT Appln. No. PCT/US06/61112 dated Sep. 25, 2008.
International Search Report and Written Opinion for PCT Appln. No. PCT/US06/61113 dated Jul. 16, 2008.
International Search Report and Written Opinion for PCT Appln. No. PCT/US08/050397 dated Jul. 11, 2008.
International Search Report and Written Opinion for PCT Appln. No. PCT/US2008/063008 dated Aug. 18, 2008.
International Search Report for PCT/US2003/21907 mailed Jun. 7, 2004.
International Search Report for PCT/US2004/040733 mailed Dec. 23, 2005.
International Search Report and Written Opinion for PCT/US2008/062873 mailed Aug. 12, 2008.
International Search Report for PCT/US2008/70647 mailed Dec. 16, 2008.
International Search Report for PCT/US2008/62875 mailed Sep. 10, 2008.

Karklin et al., "Automatic Defect Severity Scoring for 193 nm Reticle Defect Inspection," Proceedings of SPIE—The International Society for Optical Engineering, 2001, vol. 4346, No. 2, pp. 898-906.

Lu et al., "Application of Simulation Based Defect Printability Analysis for Mask Qualification Control," Proceedings of SPIE, vol. 5038, 2003, pp. 33-40.

Martino et al., "Application of the Aerial Image Measurement System (AIMS(TM)) to the Analysis of Binary Mask Imaging and Resolution Enhancement Techniques," SPIE vol. 2197, 1994, pp. 573-584.

Miller, "A New Approach for Measuring Oxide Thickness," Semiconductor International, Jul. 1995, pp. 147-148.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed., © Cambridge University Press 1988, 1992, p. 683.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Schroder et al., Corono-Oxide-Semiconductor Device Characterization, 1998, Solid-State Electronics, vol. 42, No. 4, pp. 505-512.

Schroder, "Surface voltage and surface photovoltage: history, theory and applications," Measurement Science and Technology, vol. 12, 2001, pp. R16-R31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

U.S. Appl. No. 10/677,445 (Horner et al.) entitled Methods for Non-Contacting Differential Voltage Measurements, filed Oct. 2, 2003.

U.S. Appl. No. 11/139,151 (Volk et al.) entitled Methods and Systems for Detecting Changes in Reticle Defectivity Over Time, filed May 27, 2005.

U.S. Appl. No. 12/115,830 (Su et al.) entitled Computer-Implemented Methods, Systems, and Computer-Readable Media for Determining a Model for Predicting Printability of Reticle Features on a Wafer, filed May 6, 2008.

U.S. Appl. No. 12/115,833 (Alles et al.) entitled Methods for Detecting and Classifying Defects on a Reticle, filed May 6, 2008.

U.S. Appl. No. 12/116,664 (Peterson et al.) entitled Methods and Systems for Detecting Defects in a Reticle Design Pattern, filed May 7, 2008.

U.S. Appl. No. 12/176,095 (Bhaskar et al.) entitled Methods for Generating a Standard Reference Die for Use in a Die to Standard Reference Die Inspection and Methods for Inspecting a Wafer, filed Jul. 18, 2008.

U.S. Appl. No. 12/195,024 (Florence et al.) entitled Computer-Implemented Methods for Determining if Actual Defects are Potentially Systematic Defects or Potentially Random Defects, filed Aug. 20, 2008.

U.S. Appl. No. 60/418,887 (Su et al.) entitled Methods and Systems for Inspecting Reticles Using Aerial Imaging and Die-To-Database Detection, filed Oct. 15, 2002.

U.S. Appl. No. 60/419,028 (Stokowski et al.) entitled Methods and Systems for Inspecting Reticles Using Aerial Imaging at Off-Stepper Wavelengths, filed Oct. 15, 2002.

U.S. Appl. No. 60/526,881 (Hess et al.) entitled Designer Intent, filed Dec. 4, 2003.

U.S. Appl. No. 60/681,095 (Nehmadi et al.) entitled Methods in Mask and Process Qualification, filed May 13, 2005.

U.S. Appl. No. 60/684,360 (Nehmadi et al.) entitled Design-Based Inspection, filed May 24, 2005.

Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.

Verkuil, "Rapid Contactless Method for Measuring Fixed Oxide Charge ASsociated with SIlicon Processing," IBM Technical Disclousre Bulletin, vol. 24, No. 6, 1981, pp. 3048-3053.

Volk et al. "investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Weinberg, "Tunneling of Electrons from Si into Thermally Grown SiO2," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 um Lithography," SPIE vol. 1604, 1991, pp. 106-117.

International Search Report and Written Opinion for PCT/US2008/073706 mailed Jan. 29, 2009.

International Search Report and Written Opinion for PCT/US2008/072636 mailed Jan. 29, 2009.

Allan et al., "Critical Area Extraction for Soft Fault Estimation," IEEE Transactions on Semiconductor Manufacturing, vol. 11, No. 1, Feb. 1998.

* cited by examiner

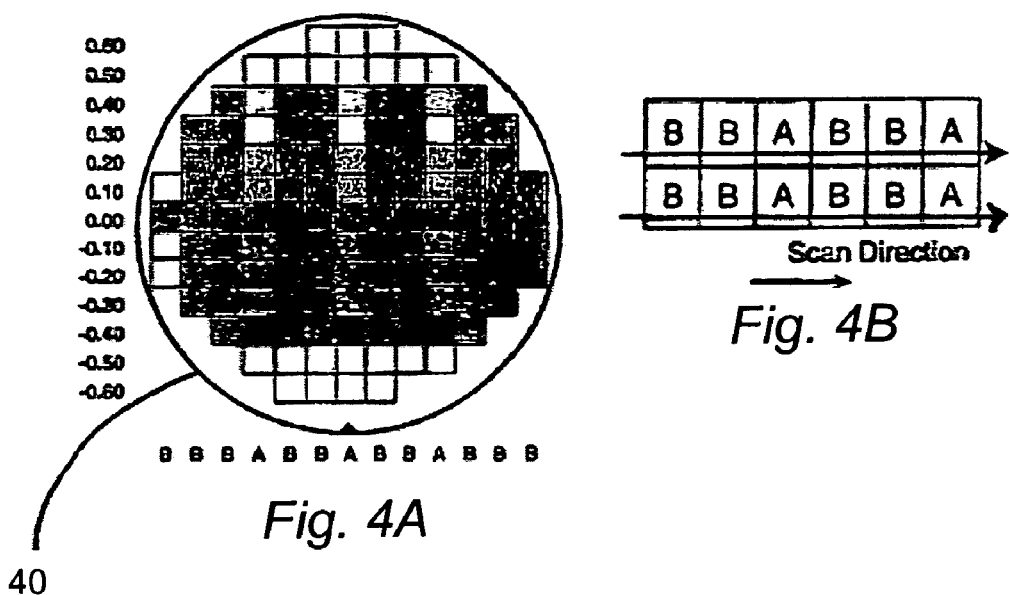
Fig. 4A
Fig. 4B
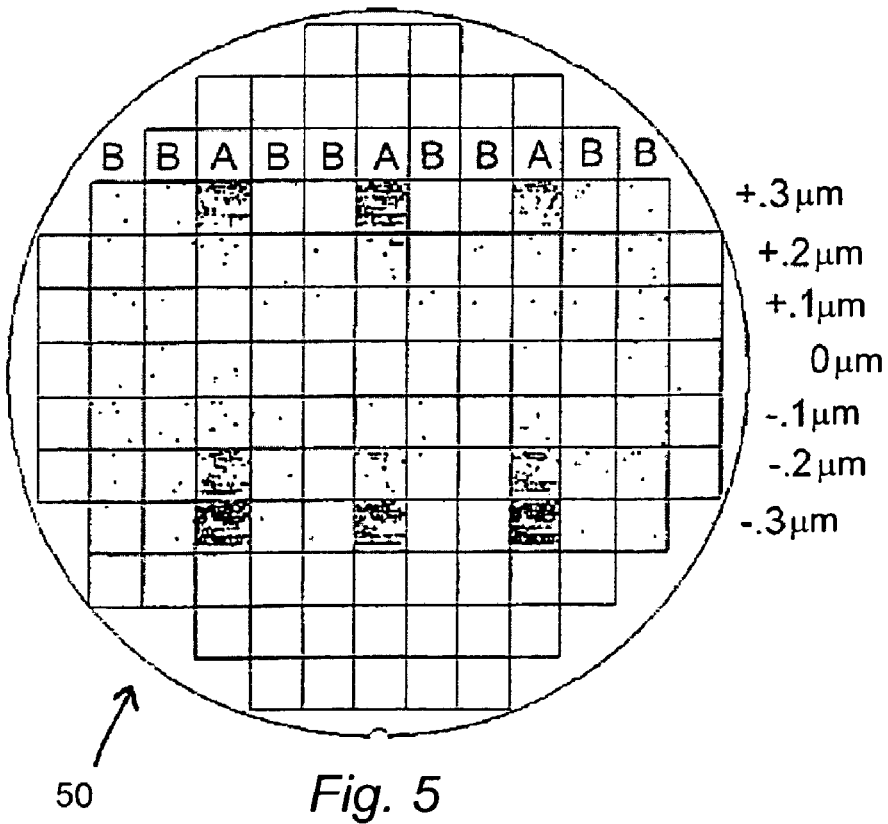
Fig. 5

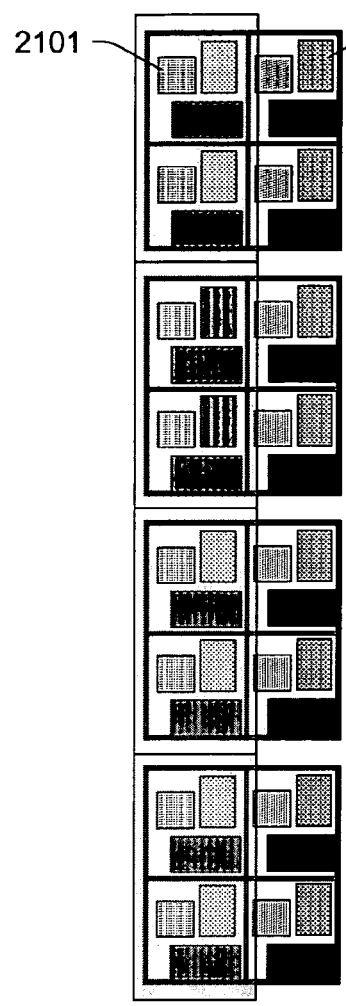
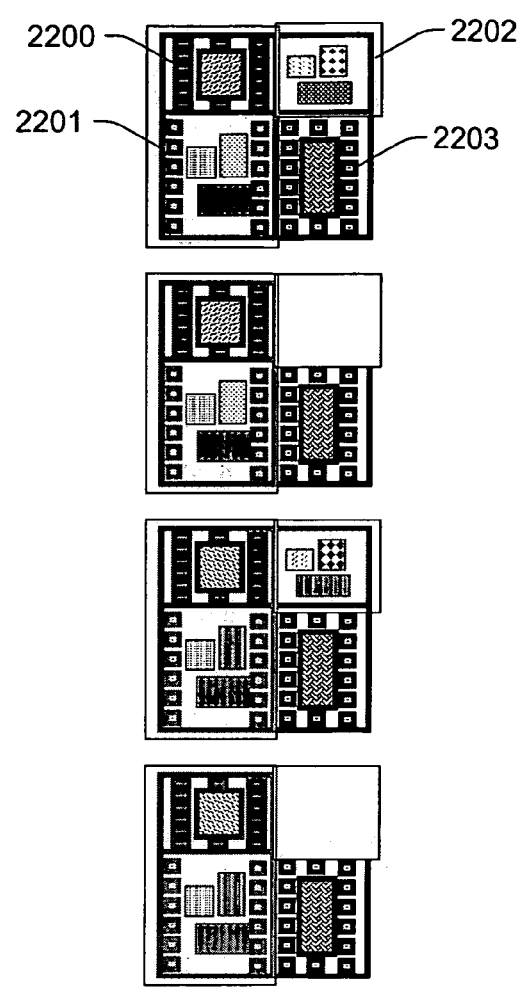
*Fig. 21*          *Fig. 22*
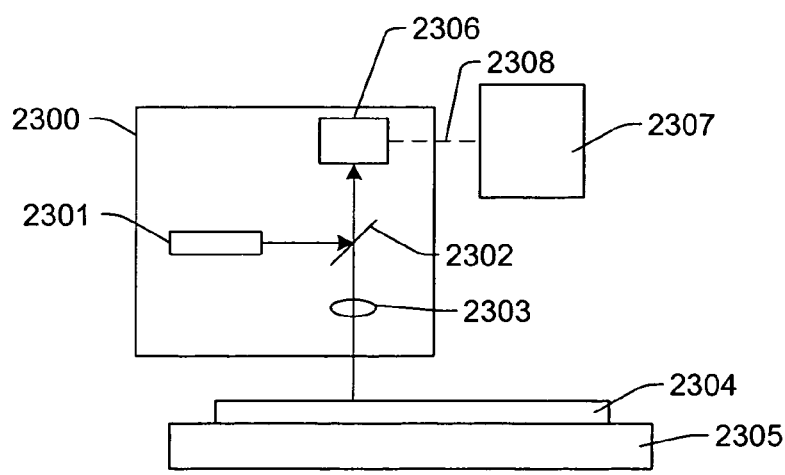
*Fig. 23*

METHODS AND SYSTEMS FOR DETECTING DEFECTS IN A RETICLE DESIGN PATTERN

PRIORITY CLAIM

This application claims priority to U.S. Provisional Application No. 60/704,806 entitled "Methods and Systems for Detecting Defects in a Reticle Design Pattern," filed Aug. 2, 2005, which is incorporated by reference as if fully set forth herein.

BACKGROUND OF THE INVENTION

1. Field of the Invention

This invention relates to methods and systems for detecting defects in a reticle design pattern. Certain embodiments relate to methods that include determining if individual defects located in a first die of a field in the reticle design data have substantially the same within die position as individual defects located in a second die of the field.

2. Description of the Related Art

The following descriptions and examples are not admitted to be prior art by virtue of their inclusion within this section.

The rapid decrease in $k_1$ (line-width=$k_1(\lambda/NA)$) in lithographic manufacture of semiconductor devices has necessitated the use of Resolution Enhancement Techniques (RET). These RET include, but are not limited to, Optical Proximity Corrections (OPC), Phase Shift Masks (PSM), and assist bar corrections. Although they are implemented in semiconductor device designs to facilitate low $k_1$ lithography, these RET make reticles more difficult and consequently more expensive to manufacture.

Semiconductor device design and reticle manufacturing quality are verified by different procedures before the reticle enters a semiconductor fabrication facility to begin production of integrated circuits. The semiconductor device design is checked by software simulation to verify that all features print correctly after lithography in manufacturing. The reticle is inspected at the mask shop for reticle defects and measured to ensure that the features are within specification. Marginal RET designs not noted by simulation checks translate into electrical failures in wafer fabrication, affect yield, and possibly remain unnoticed until wafer fabrication is complete.

Traditional methods employed in the inspection of complex mask patterns place tremendous demand on reticle inspection tools. One technique for performing image qualification entails using focus exposure matrix techniques. Performing an inspection of a conventional focus exposure matrix introduces a complication in that every exposure field is different. Die-to-die comparison is performed between adjacent local exposure fields. Any pattern change that may occur at a defocus position that is physically located farther than one exposure field from the nominal exposure field will not, therefore, be detected as different because the nominal exposure field is no longer factored in the comparison. Moreover, current reticle inspection techniques cannot detect the presence of an error in the design database. Prior art single die reticle inspection entails implementation of a design simulation technique in which a signal derived from an actual reticle is subtracted from a simulated design reference.

What is needed, therefore, is an inspection technique that is effective in locating pattern anomalies in a single die or a multi-die reticle and detecting reticle design errors resulting from errors in the design data base.

SUMMARY OF THE INVENTION

The following description of various embodiments of computer-implemented methods for detecting defects in a reticle design pattern and systems configured to detect defects in a reticle design pattern is not to be construed in any way as limiting the subject matter of the appended claims.

One embodiment relates to a computer-implemented method for detecting defects in a reticle design pattern. The method includes acquiring images of a field in the reticle design pattern. The images illustrate how the field will be printed on a wafer at different values of one or more parameters of a wafer printing process. The field includes a first die and a second die. The method also includes detecting defects in the field based on a comparison of two or more of the images corresponding to two or more of the different values. In addition, the method includes determining if individual defects located in the first die have substantially the same within die position as individual defects located in the second die.

In some embodiments, the substantially the same within die position includes a range of within die positions defined by a single within die position and a predetermined tolerance for acceptable positional variance. In another embodiment, the determining step may include determining if the individual defects in the first die having substantially the same within die position as the individual defects located in the second die have one or more different characteristics. Such an embodiment also includes determining if the individual defects in the first or second die are random defects obscuring a defect in the reticle design pattern.

In one embodiment, the method also includes assigning a priority to the individual defects based on results of the determining step. In another embodiment, the method includes assigning a higher priority to the individual defects that are located in the first and second die at substantially the same within die position than the individual defects that are not located in the first and second die at substantially the same within die position. In a further embodiment, the method includes assigning a composite priority to the individual defects based on results of the determining step in combination with the different values corresponding to the images of the field.

In an additional embodiment, the method includes determining if the individual defects that are located in the first and second die at substantially the same within die position have a characteristic that is substantially the same. In one such embodiment, the characteristic qualifies as being substantially the same if a value of the characteristic is within a range of values for the characteristic. The range may be defined by a single value for the characteristic and a predetermined tolerance for acceptable characteristic variance. In another embodiment, the method includes assigning a higher priority to the individual defects that are located in the first and second die at substantially the same within die position and have one or more characteristics that are substantially the same than a priority assigned to the individual defects that are located in the first and second die at substantially the same within die position and exhibit differences in the one or more characteristics.

In one embodiment, the method includes selecting the first and second die within the field based on locations of the first and second die within the field. In a different embodiment, the field may include die for different devices. In one such embodiment, the method may include lo selecting the first and second die within the field based on the different devices associated with the die.

In one embodiment, a sensitivity of the determining step in a first region of the first and second die is different than a sensitivity of the determining step in a second region of the first and second die. Another embodiment of the method includes filtering the individual defects based on results of the determining step.

In one embodiment, the images of the field include images of the reticle design pattern printed on a wafer using the wafer printing process. In a different embodiment, the images of the field include aerial images of the reticle design pattern printed on the reticle. In other embodiments, the images of the field include simulated images. Each of the embodiments of the method described above may include any other step(s) described herein.

Another embodiment relates to a system configured to detect defects in a reticle design pattern. The system includes an optical subsystem that is configured to acquire images of a field in the reticle design pattern. The images illustrate how the field will be printed on a wafer at different values of one or more parameters of a wafer printing process. The field includes a first die and a second die. The system also includes a processor coupled to the optical subsystem. The processor is configured to detect defects in the field based on a comparison of two or more of the images corresponding to two or more of the different values. The processor is also configured to determine if individual defects located in the first die have substantially the same within die position as individual defects located in the second die.

In one embodiment, the optical subsystem is configured to acquire the images by imaging a wafer on which the reticle design pattern is printed using the wafer printing process. In another embodiment, the optical subsystem is configured as an aerial imaging measurement system. In one such embodiment, the aerial imaging measurement system includes sensors coupled to a substrate and positioned at different heights with respect to a reticle on which the reticle design pattern is formed. The sensors are configured to acquire the images. Each of the embodiments of the system described above may be further configured as described herein.

An additional embodiment relates to a different system that is configured to detect defects in a reticle design pattern. This system includes a simulation engine configured to generate simulated images of a field in the reticle design pattern. The simulated images illustrate how the field will be printed on a wafer at different values of one or more parameters of a wafer printing process. The field includes a first die and a second die. The system also includes a processor coupled to the simulation engine. The processor is configured to detect defects in the field based-on a comparison of two or more of the simulated images corresponding to two or more of the different values. The processor is also configured to determine if individual defects located in the first die have substantially the same within die position as individual defects located in the second die. This system embodiment may also be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 4A shows a focus-modulated wafer surface printed with a reticle that is to be qualified according to the "BBA" column pattern of FIG. 2;

FIG. 4B is an enlarged view of several contiguous exposure field regions of the wafer surface of FIG. 4A;

FIG. 5 is a diagram of a defect data map of a scanned test wafer;

FIG. 21 is a schematic diagram illustrating a top view of multiple die in a field in which a portion of the multiple die are selected based on locations of the multiple die within the field;

FIG. 22 is a schematic diagram illustrating a top view of a field that includes die for different devices in which a portion of the die are selected based on the different devices associated with the die;

FIGS. 23-24 are schematic diagrams illustrating a side cross-sectional view of various embodiments of a system that is configured to detect defects in a reticle design pattern.

Figure 1A:
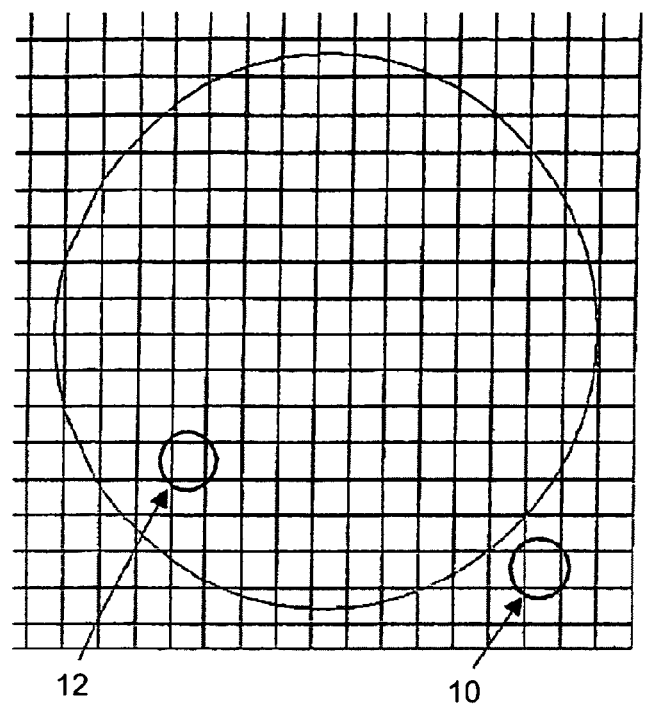
FIGS. 1A and 1B show, respectively, single die reticle and multi-die reticle wafer layouts.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "reticle" is used interchangeably with the term "mask." In addition, the term "defect" is used interchangeably with the term "anomaly."

A preferred embodiment implements modulation of focus of light illuminating reticles, each of which is used to expose by a step and repeat or a step and scan process a top layer of photoresist covering a test wafer. The reticles are printed on optimized film stacks, the type of optimization depending on the type of process level, which includes contact or via, gate, and trench. The base film stack is preferably a simple thermally grown or deposited stack of 1050X oxide covered by 320X SiON or any other base film stack known in the art. However, the reticles to be tested could also be printed on product wafers on which the "Process of Record" stack for the mask layer being tested is formed.

Figure 1B:
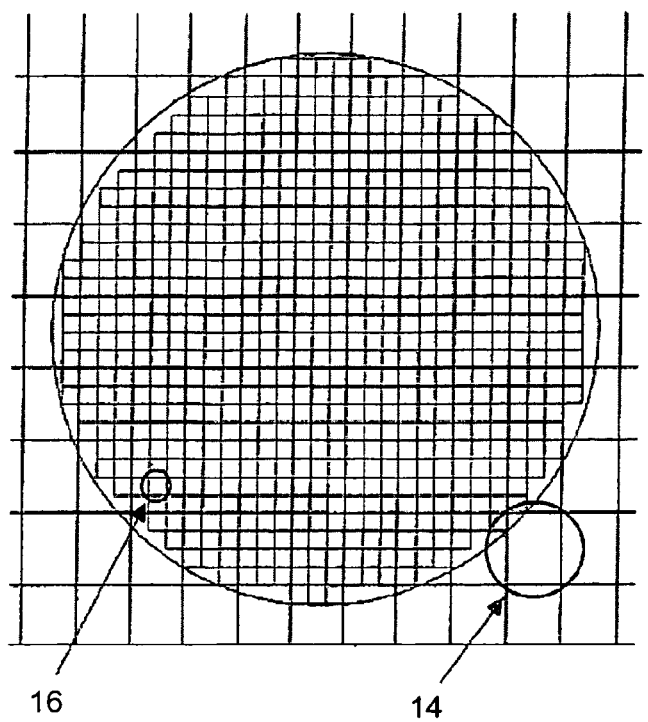

FIGS. 1A and 1B show, respectively, prior art single die reticle (exposure field 10 contains one unique die 12) and prior art multi-die reticle (array of multiple rows and columns of nominally identical die where exposure field 14 contains multiple die 16) wafer layouts and indicate their exposure field and die boundary dimensions. After photoresist patterning, inspection is preferably, but need not be, performed after etching on the SiON/oxide base film stack and stripping the photoresist: Inspecting an etched pattern usually yields a more sensitive inspection.

The exposure layout of the test wafer entails creating by a step and repeat exposure process an array of exposure field regions arranged in rows and columns. A lithographic parameter such as an illumination operating variable is modulated by rows but in only certain columns. Adjacent columns modulated by the operating variable are separated by at least one column not modulated by the operating variable. A typical and preferred operating variable is illumination focus.

Figure 2:
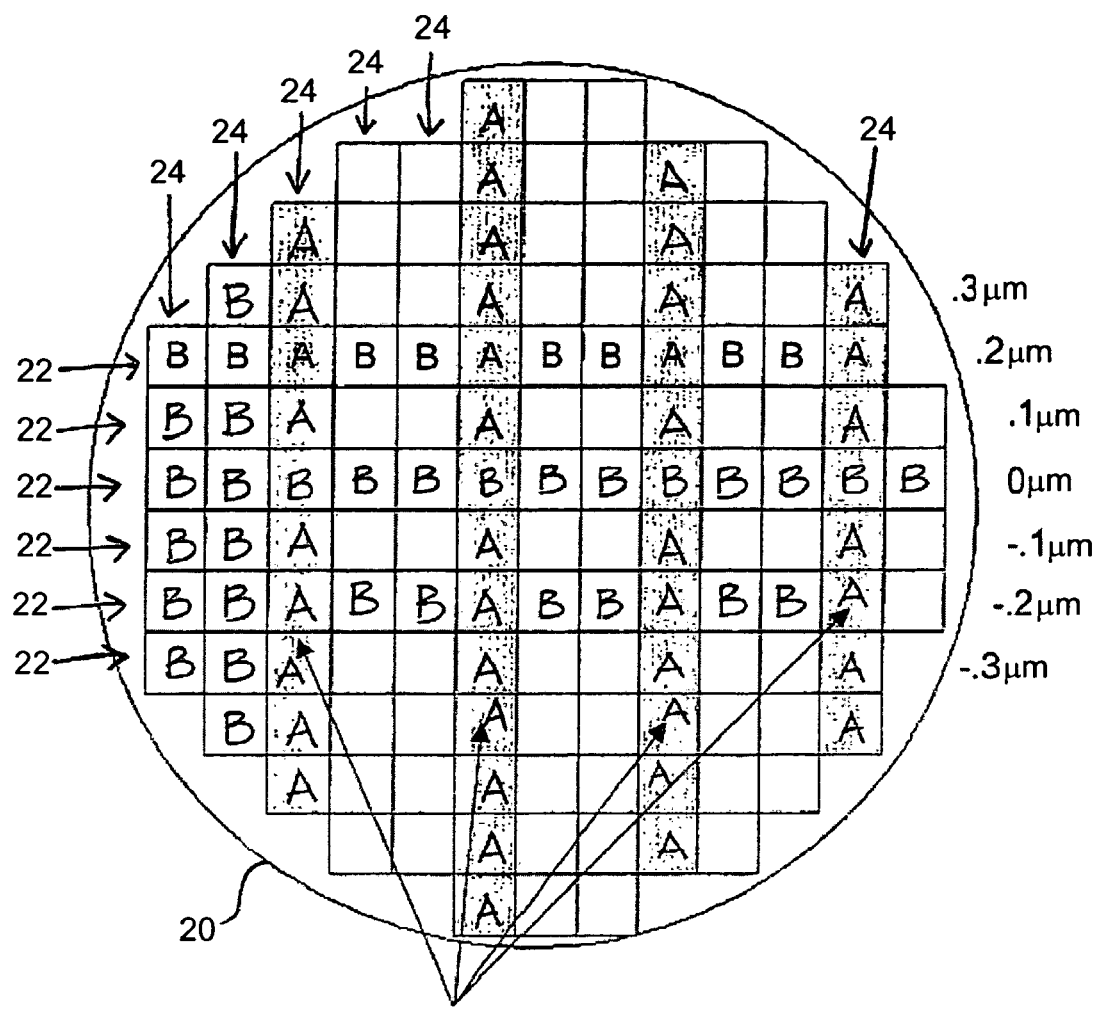
FIG. 2 is a schematic diagram of a wafer, with its surface subdivided into columns representing a "BBA" exposure field layout.

FIG. 2 shows an exposure layout for an exemplary 300 mm test wafer 20 in which illumination focus is progressively modulated in 0.1 μm increments of defocus in rows 22 positioned either direction away from a constant focus, constant exposure center row (0 μm). Four sets of three columns 24 each include two leading "B" columns of constant focus and constant exposure and one trailing "A" column of the focus condition corresponding to the row with which the "A" column intersects. (For purposes of visual clarity, only some of the exposure field regions are marked with "A" or "B.") The three-column set layout affords double detection of events and subsequent arbitration of die where an event is located. Because the three-column set includes two "B" column dies, there is double detection of good features. A defect inspection tool can determine a difference between a column "A" die and either of the column "B" dies and thereby isolate defects, particularly transient defects. Skilled persons will appreciate that the exposure layout of FIG. 2 can be used on 200 mm wafers as well.

Figure 3:
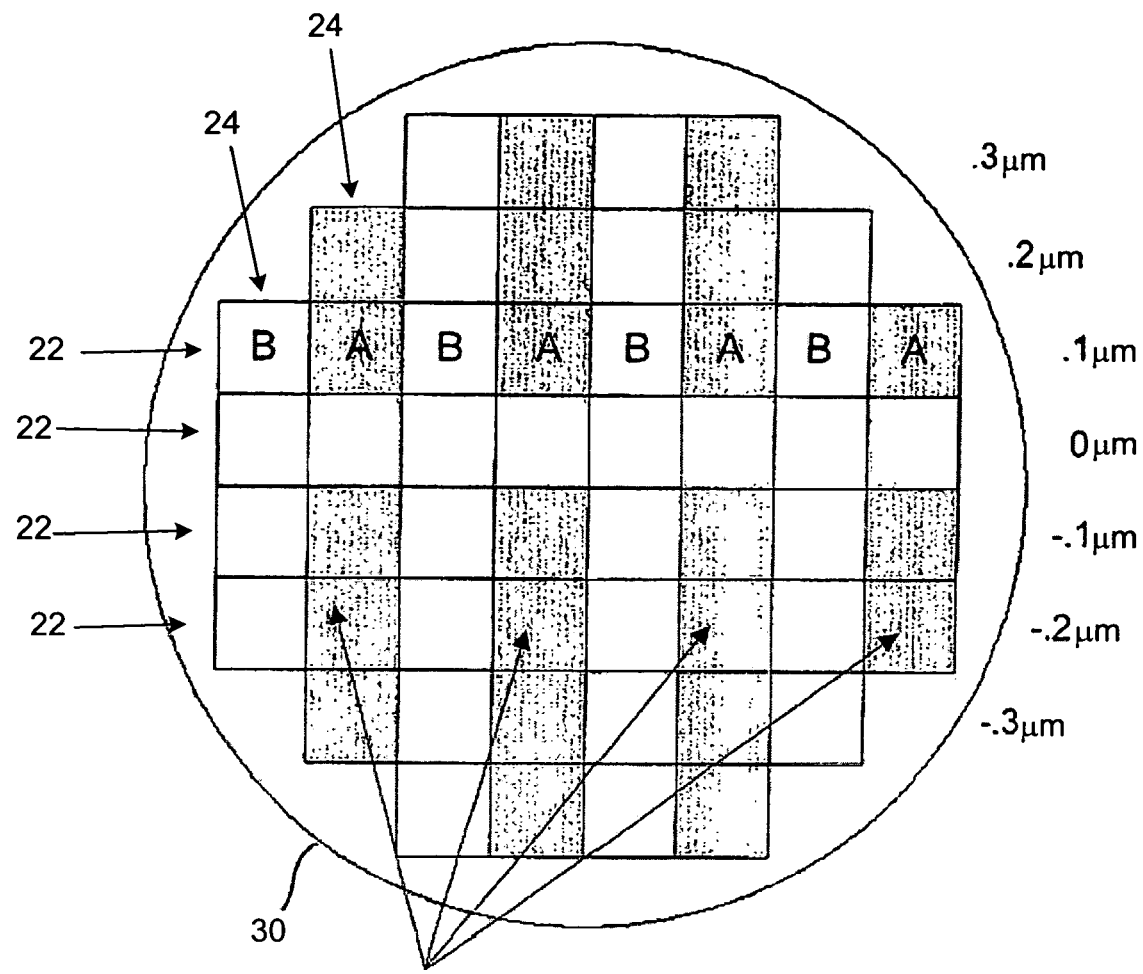
FIG. 3 is a schematic diagram of a wafer, with its surface subdivided into columns representing a "BA" exposure field layout.

FIG. 3 is an exposure layout shown for an exemplary 200 mm test wafer 30 in which focus is progressively modulated as in the 300 mm test wafer of FIG. 2, but with one exception. The exception is that there are four sets of two columns 24 alternating between a leading "B" column of constant focus, constant exposure and a trailing "A" column of the focus condition corresponding to the row 22 with which the "A" column intersects. The two-column set layout affords single detection of events with possible incorrect event location.

Skilled persons will appreciate that the process window qualification procedure may also be adapted for other lithographic parameters, such as optimizing partial coherence (sigma), numerical aperture (NA), and various illumination modes. Focus is a preferred illumination operating variable because it is the parameter most likely to vary daily from tool to tool. Optimizing other lithographic parameters will depend on the ability of the exposure tool to actively modulate the desired parameter for different exposures. Examples of design of experiment work that may be valuable to a lithography engineer include optimizing a sigma setting that balances tradeoffs between isolated contacts or vias and dense contacts or vias, optimizing the numerical aperture setting to allow maximum depth of field while retaining an acceptable process window, and choosing an illuminator that yields maximum process latitude for the pattern type being printed.

Figure 6:
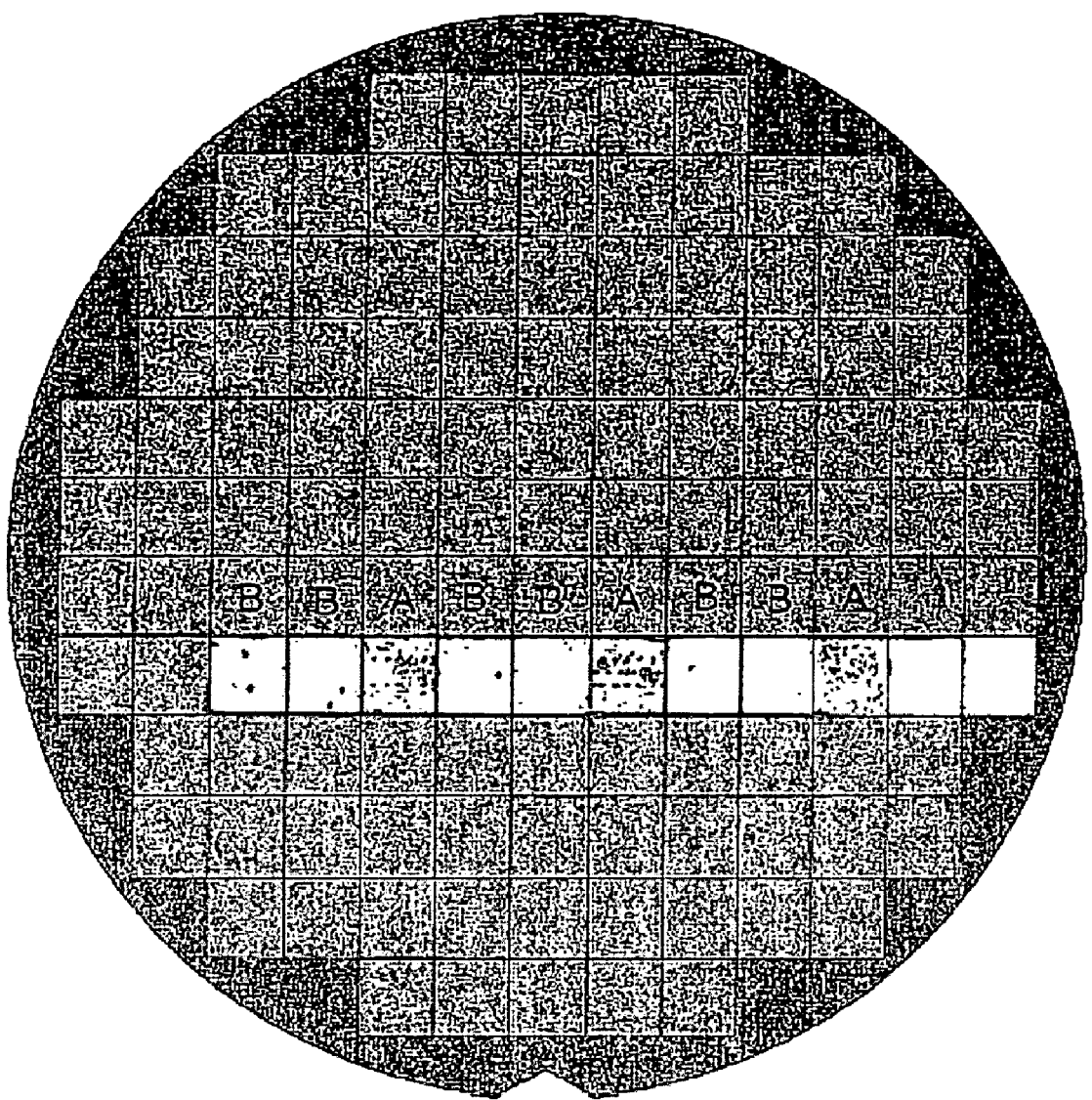
FIG. 6 is a diagram showing the defect event counts in the exposure field regions of the −0.2 μm defocus row of the test wafer of FIG. 5, from which exposure field regions hard repetitive defects have been removed.

FIGS. 4-12 illustrate the steps of sorting pattern anomalies from a test wafer in accordance with the invention. FIG. 4A shows a focus-modulated wafer 40 printed with a reticle that is to be qualified according to a "BBA" column pattern of a type shown in FIG. 2. Modulating the focus amplifies the impact of RET design rule errors. FIG. 4B is an enlarged view of portions of two rows including six columns of exposure field regions to show a preferred scan direction for inspecting the "BBA" column pattern. FIG. 5 is a diagram of a defect map 50 of a scanned test wafer exhibiting increasing defect counts of exposure field regions in rows representing increasing amounts of defocus in 0.1 μm increments relative to a zero defocus row. Defect map 50 of the wafer can contain thousands of defects, including a combination of random defects and repeating defects. FIG. 6 shows the defect event counts in the exposure field regions of the −0.2 μm defocus row of defect map 50 of FIG. 5. The "A" column exposure regions exhibit greater numbers of defect event counts than those exhibited in the "B" column exposure regions, from which "A" and "B" column exposure regions hard repetitive defects have been removed.

Figure 7:
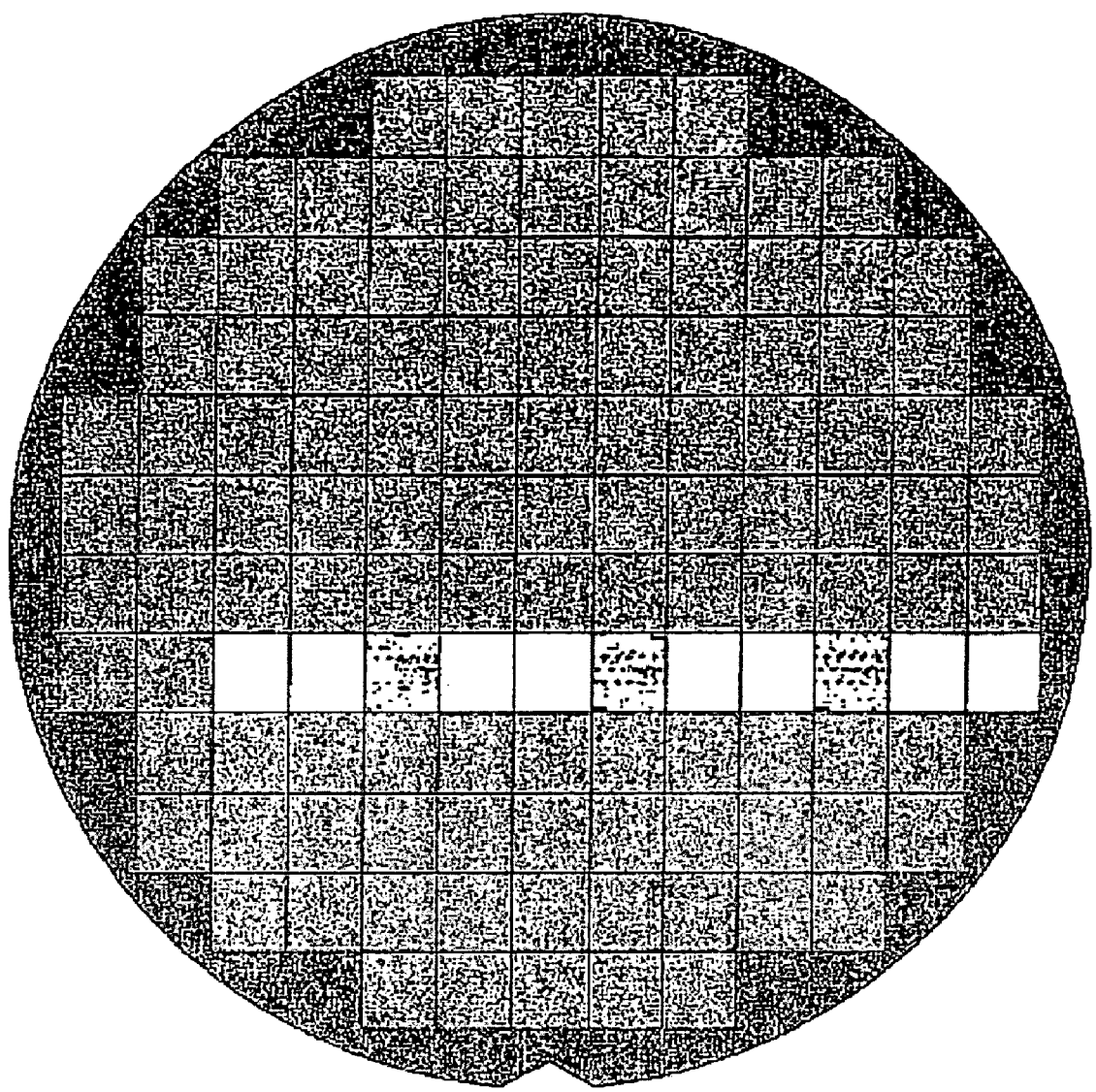
FIG. 7 is a diagram showing the isolation of defect event counts in the defect data files of the "A" columns of FIG. 6.
Figure 8:
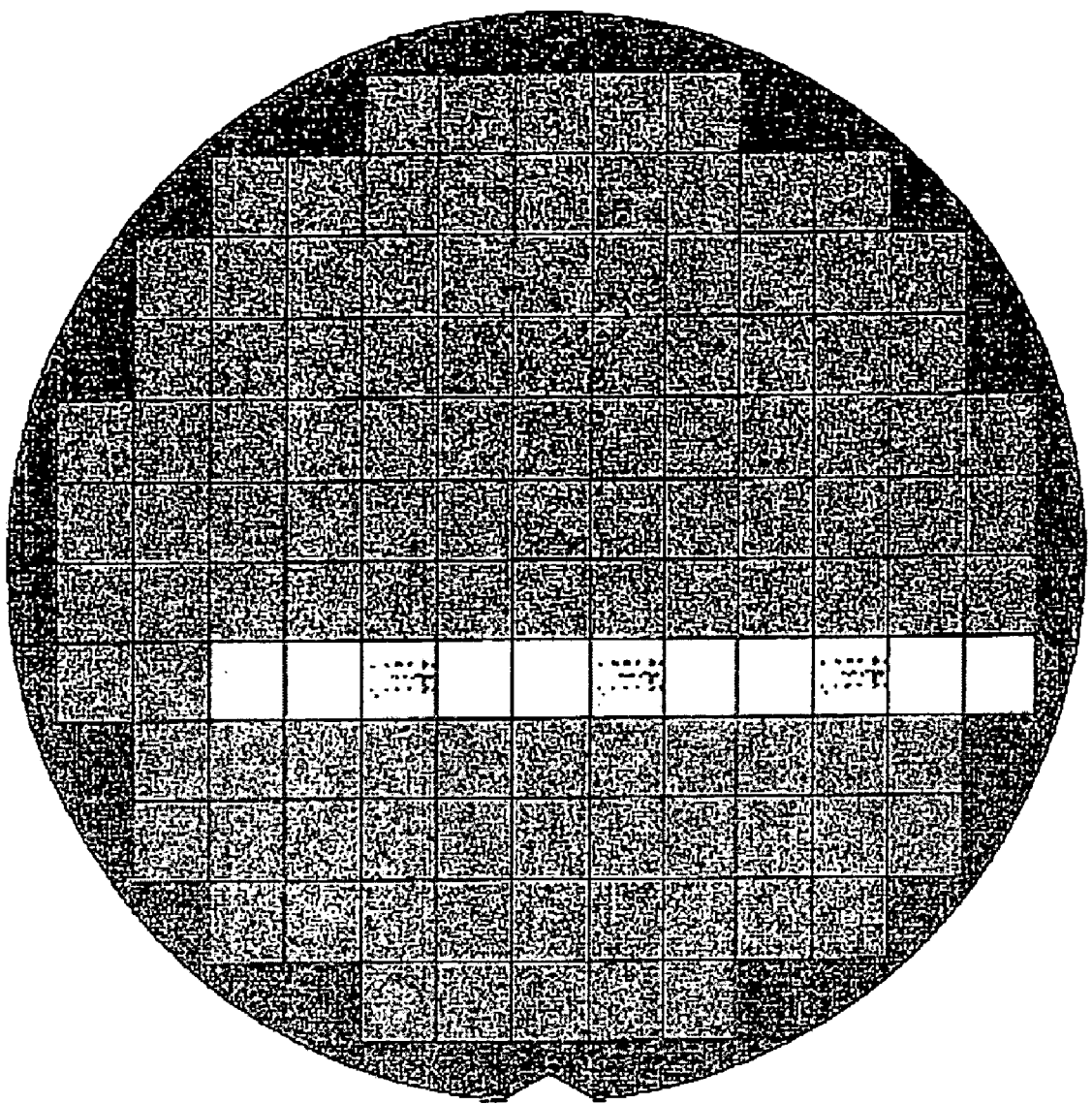
FIG. 8 is a diagram showing the isolation of transient repeater defects present in a stack of the defect data files of the three "A" column exposure field regions of FIG. 7.
Figure 9:
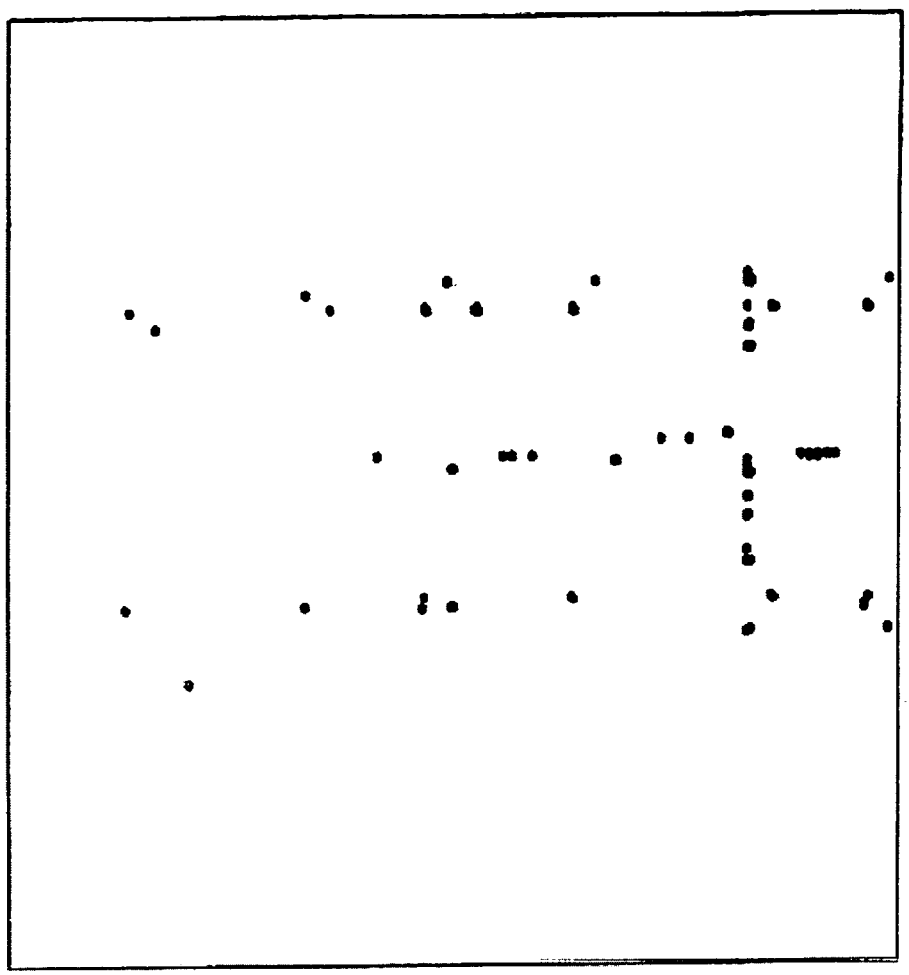
FIG. 9 is an enlarged diagram of the stack of defect data files in the "A" column exposure field regions of FIG. 8.

FIG. 7 shows the isolation of defect event counts in the defect data files of the "A" column exposure field regions of the defect map of FIG. 6. FIG. 8 shows the isolation of transient repeater defects present in a stack of the defect data files of the three "A" column exposure field regions of the test wafer of FIG. 7. This isolation is accomplished by advanced repeating defect algorithms, such as those implemented in KLArity® Defect inspection software available from KLA-Tencor Corporation. FIG. 9 is an enlarged view of the stack-of the defect data files of the transient repeater defects in the "A" column exposure field regions of FIG. 8. The defect events shown in FIG. 9 appear on all of the "A" exposure field regions, so any of the "A" regions in the −0.2 μm defocus row may be used to view the defects.

The above-described defect or pattern anomaly isolation process is carried out for the reference (0 μm defocus) row and each of the defocus rows of the process window qualification test wafer, not just the −0.2 μm defocus row described above. Exposure pattern or die stacking performed for each row reduces to several hundred the number of repeating pattern anomalies. Certain of these repeating pattern anomalies are not of interest because they reside in non-critical areas or represent uniform critical dimension variations caused by the focus modulation. After the transient repeater defects have been sorted, the test wafer exposure fields are analyzed to identify the critical repeating pattern anomalies and those associated with RET design rule violations. The objective is to send only a few repeating pattern anomalies to a defect review or analysis tool such as a critical dimension or defect review scanning electron microscope (SEM) or atomic force microscope (AFM) for further analysis. Coordinates of the defect locations used for further analysis of the defects by the defect review or analysis tool can be recorded automatically using data obtained in accordance with the processes described herein. Defects for defect review or analysis can be further selected based on position within the die and criticality as established by the design file for the reticle (e.g., GDS2, GDS2 derivative, or equivalent data type).

Figure 10:
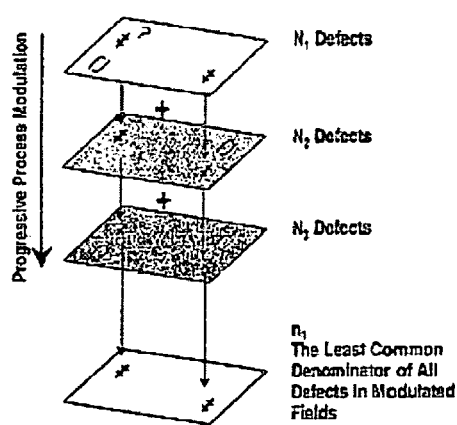
FIG. 10 is a diagram that is useful in explaining the analysis of identifying critical pattern anomalies.

FIG. 10 is a diagram that illustrates the analytical approach used in identifying critical pattern anomalies. The method of analysis enables qualifying single die reticles and detecting design pattern defects. The pattern anomaly analysis can be summarized as follows. FIG. 10 shows three levels $N_1$, $N_2$, and $N_3$ of one of the "A" column exposure field regions of a die within a 0.3 μm defocus range composed of three 0.1 μm defocus increments. Each of $N_1$, $N_2$, and $N_3$ represents a data file of positions where defects were found upon completion of the subtraction and arbitration processes described above. FIG. 8 illustrates the database that is the result of the arbitration process illustrated by FIG. 7. The exposure field regions of each "A" column are stacked within the range of defocus increments to determine the locations of design pattern anomalies for increasing amounts of defocus relative to the reference die row of zero defocus. This is accomplished by taking and comparing for a column the differences between different pairs of data files corresponding to exposure field regions located on either side of the reference row. Skilled persons will appreciate that a reference need not be a zero defocus value but could be a value that is appropriate for the lithographic operating variable selected.

FIG. 10 shows that the difference between the reference row and row $N_1$ (+0.1 μm defocus) produces anomalies at four locations; the difference between the reference row and row $N_2$ (+0.2 μm defocus) produces anomalies at three locations, two of which anomalies are common to anomalies in level $N_1$; and the difference between the reference row and row $N_3$ (+0.3 μm defocus) produces anomalies at four locations, three of which anomalies are common to anomalies in level $N_2$ and one of which is common to an anomaly in level $N_1$. FIG. 10 shows a level $n_1$, which represents the least common denominator of all defects in the focus modulated exposure field regions. The defects shown in level $n_1$ represent the most marginal, but are not necessarily the most critical, pattern anomalies. Stacking the difference values of the various defocus levels gives an indication of the weakest features, which include those common to all modulated exposure field regions and those that appear in the level $N_1$ (lowest defocus) modulated exposure field region. The number of occurrences and location of a design pattern anomaly contribute to its critical status.

The "A" column repetitive anomalies that offer the smallest process window are the most important ones. The "A" column repetitive anomalies that appear in row $N_1$ represent, therefore, the weakest features. Selecting the "A" column repetitive anomalies that are common to all modulated fields identifies these weakest features. Reviewing and manually classifying the weakest features indicates the locations of the weaker geometries in the design pattern layout. Weakest features can also be analyzed as described in International Publication No. WO 00/36525 by Glasser et al., published Jun. 22, 2000, which is incorporated by reference as if fully set forth herein. Aligning the file data of isolated defects relative to the design file can be accomplished in a manner described in pending U.S. patent application Ser. No. 10/029,521, filed Dec. 21, 2001, which is also incorporated by reference as if fully set forth herein.

Figure 11:
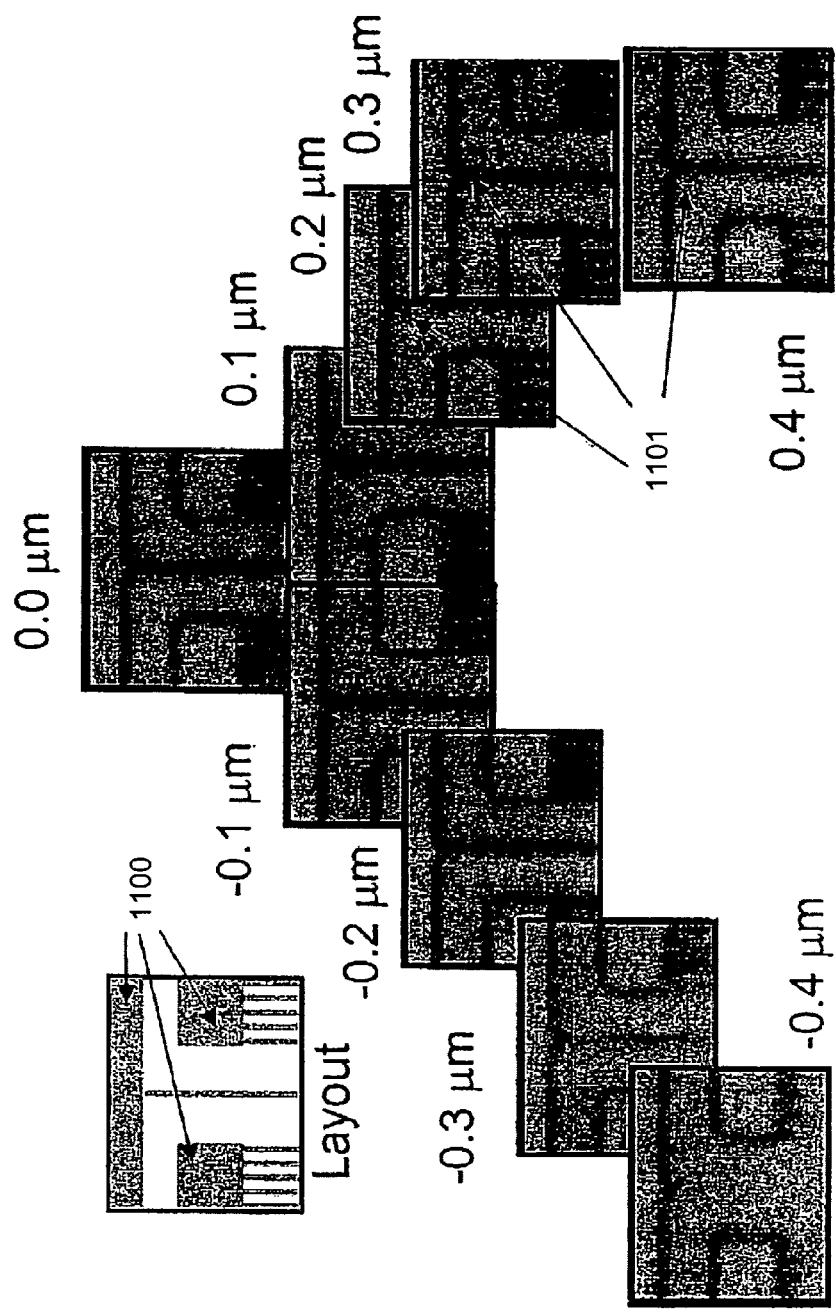
FIG. 11 is a series of optical images showing for a particular location in an exposure field the effects of 0.1 μm defocus increments in a ±0.4 μm defocus range.

FIG. 11 shows a series of optical images of the same location in an exposure field region for each of 0.1 μm defocus increments in a ±0.4 μm defocus range. FIG. 11 also shows the design pattern layout including polysilicon areas 1100 to which the images nominally correspond. Analysis of FIG. 11 reveals progressive line thinning 1101 for increasing defocus increments from zero defocus to +0.4 μm and loss of feature altogether for increasing defocus increments from zero defocus to −0.4 μm.

Figure 12:
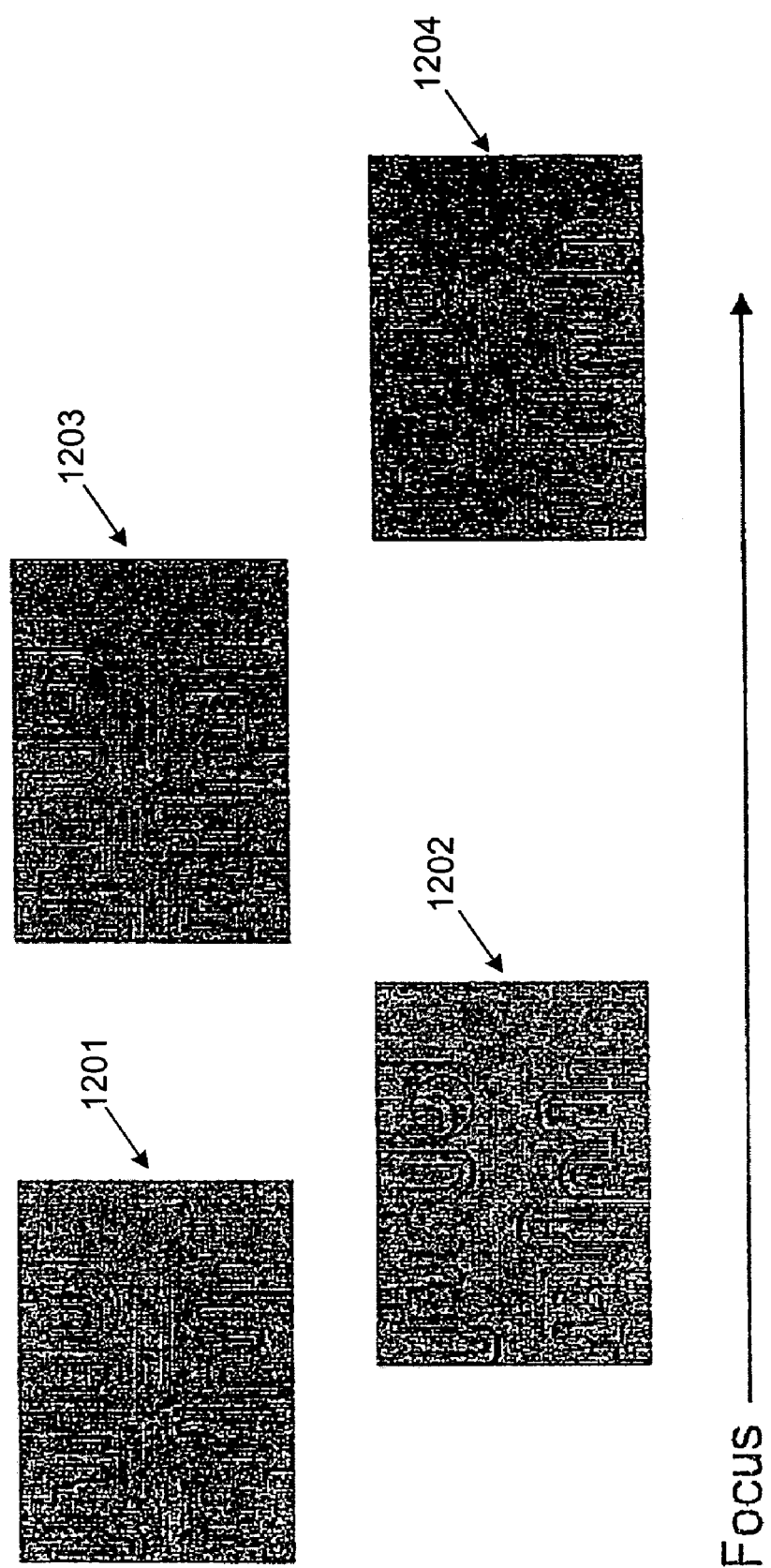
FIG. 12 is a series of optical images of a polysilicon wafer pattern progressively losing line fidelity for increasing amounts of illumination defocus.

FIG. 12 shows a series of optical images of a polysilicon wafer pattern progressively losing line pattern fidelity of an encircled area for increasing amounts of illumination defocus. Leftmost image 1201 represents a best focus condition, and rightmost image 1204 represents a defocus condition sufficient to produce a break in the line pattern. Images 1202 and 1203 represent images produced at defocus conditions between best focus and the focus condition of image 1204.

The above described embodiment entails exposing a test wafer to multiple reticle pattern images formed by different values of focus of light illuminating the reticle. The method has, however, general applicability in qualifying a pattern, patterning process, or patterning apparatus used in the fabrication of microlithographic patterns for producing microelectronic devices.

For example, the process of comparing images formed by different values of an illumination operating variable as described with reference to FIGS. 6-12 can be carried out on stored image data acquired by practice of AIMS techniques, DRC techniques, or optical rule check (ORC) techniques, which are a variation of the DRC techniques. The image data can represent a design pattern of a mask, reticle, or other patterned specimen. The AIMS technique and DRC technique entail storing data corresponding to, respectively, aerial images and computed or simulated images of the design pattern for each of the multiple values of an illumination operating variable. Discussions regarding use of the AIMS and DRC techniques can be found in U.S. Pat. No. 6,268,093 to Kenan et al. and U.S. Pat. No. 6,373,975 to Bula et al., respectively. The disclosures of those patents are hereby incorporated by reference in their entireties, and the methods described herein could be used to enhance the processes and apparatus set forth in those disclosures. Examples of evaluating a reticle or mask using simulated images of the reticle at different process parameters are illustrated in a commonly assigned copending application by Howard et al. having U.S. Ser. No. 10/793,599, filed Mar. 4, 2004, which claims priority to U.S. Ser. No. 60/451,707, filed Mar. 4, 2003, both of which are incorporated by reference as if fully set forth herein and for all purposes. The methods described herein may include any of the steps or embodiments described by Howard et al.

Figure 13:
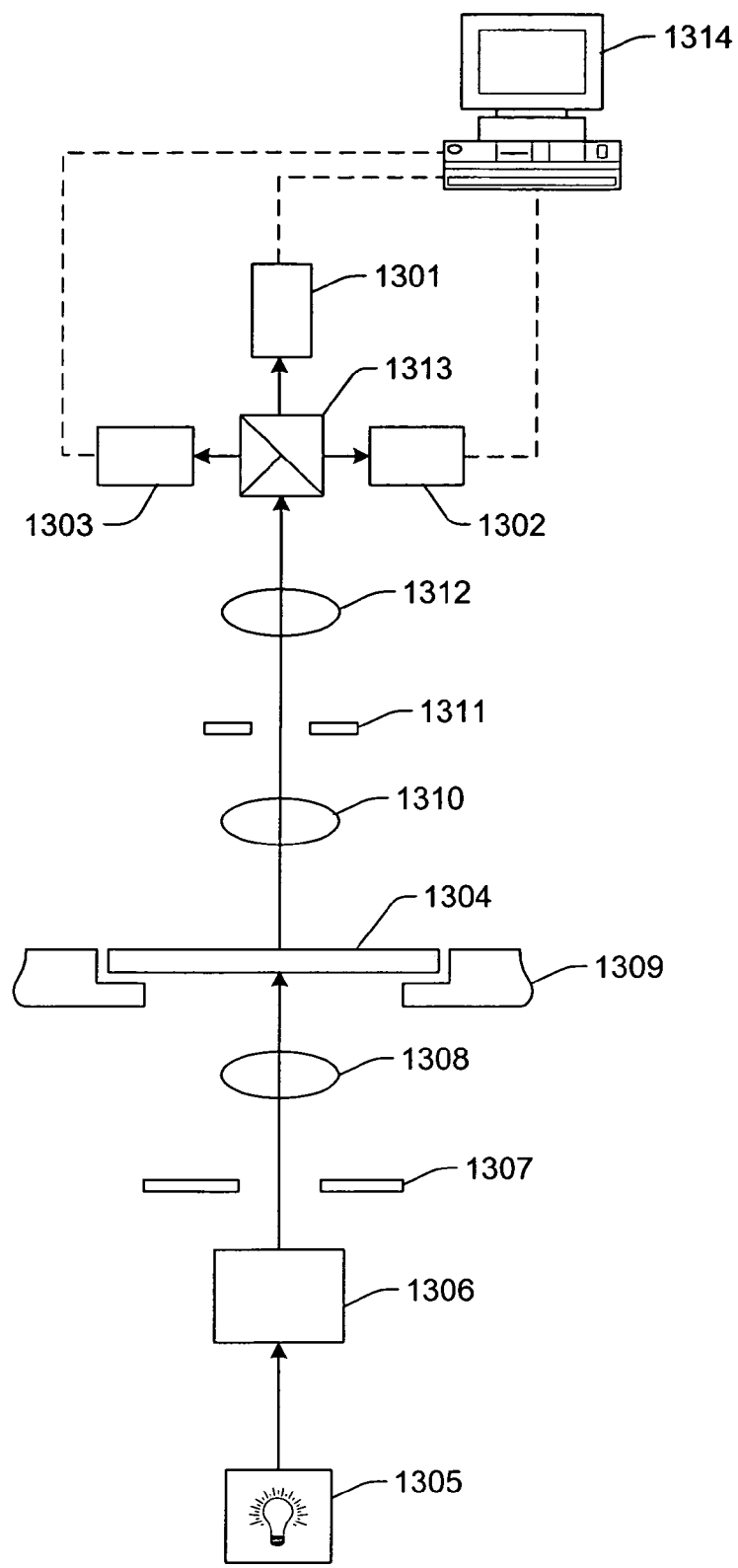
FIG. 13 is a schematic diagram of an apparatus that can be used in connection with an AIMS embodiment of the invention.

One possible manner of implementing the methods described herein using an AIMS technique may be better understood by reference to FIG. 13. In FIG. 13, a system is shown having three detectors, i.e., detectors 1301, 1302 and 1303. Each of these detectors may preferably be set at a different focal position. For example, detector 1301 could be at zero defocus, detector 1302 could be at +0.2 defocus, and detector 1303 could be at minus 0.2 defocus. Of course, these levels of defocus are only examples. Any suitable range of levels of defocus could be used, and such levels would be optimized empirically. It is not necessary to use a detector having zero defocus, for example, and all of the detectors could be set at varying levels of positive defocus, or at mixed levels of positive and negative defocus.

Sample 1304 is preferably a mask or reticle. As sample 1304 is exposed to illumination source 1305, an aerial image is detected at the three detectors. Because of their different focal positions, the aerial images at each detector will have different levels of defocus. Images having varying levels of defocus may be compared and analyzed using any of the techniques previously set forth herein. In a preferred embodiment, signals taken from a first detector, such as detector 1301, are compared to signals taken from a second detector, such as detector 1302, continuously as sample 1304 is inspected. This is only one example, of course, any pairs of detectors could be compared. Alternatively, comparisons could be made between detectors and mathematical combinations of other detectors (such as a pixel by pixel average between a pair of detectors, or a difference between another pair of detectors). Preferably, the levels of defocus and/or the types of comparisons between the signals from the various detectors (or combinations thereof) are selected to provide the user with information regarding RET defects and the appearance of such defects across a process window.

In the embodiment shown in FIG. 13, it is possible to simultaneously perform a conventional inspection and a process window qualification. The purpose and methodology of the process window qualification (to find RET defects and the like) has already been described herein, and is further described hereinafter. The purpose of the conventional inspection is to find other types of defects, such as defects resulting from reticle manufacturing errors and/or from contaminants on the reticle. A method of such a conventional inspection is described in U.S. Pat. No. 6,268,093 to Kenan et al., which is mentioned above and incorporated by reference therein. Other suitable methods of performing such inspections are described in more detail in a commonly assigned copending application by Stokowski et al. having U.S. Ser. No. 10/679,617, filed Oct. 6, 2003, which claims priority to U.S. Ser. No. 60/418,994, filed Oct. 15, 2002, both of which are incorporated by reference herein in their entirety and for all purposes. Such suitable methods include, without limitation, a die-to-database inspection in which the reticle is inspected by comparison against a rendered database from which the reticle was created.

In a preferred embodiment, the conventional inspection is done by comparing signals from the same detector taken at nominally identical portions of different dies. This inspection process works well for multi-die reticles. The process window qualification is performed substantially simultaneously, and may be achieved as already described herein by comparing images at varying levels of defocus for each die. So the conventional inspection might be achieved by comparing images from a first die on sample 1304 to images of a second die on sample 1304, wherein each image is detected using detector 1301. At substantially the same time as the images of each such die are collected for purposes of the conventional inspection, for each such die an image from detector 1301 and/or detector 1302 or detector 1303, is also compared to an image of that same die taken at a different focal position (for example from another of detectors 1301, 1302 and/or 1303, or any mathematical combination thereon). Thus, the conventional inspection and process window qualification may be performed substantially simultaneously.

If desired, the processing of the data from the conventional inspection and from the process window qualification could be performed on the same computer by using parallel processing. A suitable architecture and methodology are described in more detail in a commonly assigned copending application by Goldberg et al. having U.S. Ser. No. 09/449,022, filed Nov. 24, 1999, and incorporated by reference herein in its entirety and for all purposes.

In yet another embodiment of the invention, and in accordance with the above description of the example shown in FIG. 13, a single die reticle could be provided as sample 1304, and only a process window qualification may be performed using the apparatus shown in FIG. 13. Such a technique may be desirable for all types of reticles, and may be particularly desirable for single die reticles. This is because the apparatus shown in FIG. 13 is in many ways inferior to other types of inspection systems, such as the 3XX and 5XX series commercially available from KLA-Tencor Corp of San Jose, Calif. Thus, it may be desirable to find conventional defects using the KLA-Tencor tools, and then inspect the same reticle again in an aerial image mode to locate RET defects by varying the process window. As mentioned above, this may be particularly desirable where sample 1304 is a single die reticle. This avoids the need to render the design database in a mode suitable for comparison against the aerial image. Instead, the aerial image is used only for purposes of finding RET defects, and the conventional inspection is done using a more accurate tool which can directly compare the actual image of the reticle to the rendered database (including the OPC features present therein).

Of course, if a suitably rendered database is available for comparison against the AIMS image (rendered using the techniques described, for example, in the application by Stokowski et al., as mentioned above), a die-to-database inspection could be done using an AIMS tool such as that shown in FIG. 13. In such a case, it is possible to also do the inspection for RET defects by using a comparison against the rendered database. For example, the conventional inspection could be performed by comparing images from a detector at zero defocus to images rendered from, the database, also at zero defocus. The RET defects could then be found by comparing the images from one or more detectors, at varying levels of defocus, against the rendered database at zero defocus. Or the database could also be, through-simulation, rendered in a manner that is consistent with a given level of defocus. In either situation, the methods described herein could be applied to find RET defects.

The present invention is not limited to just finding RET defects by varying the level of defocus. As noted above, varying sigma and/or the numerical aperture (NA) of the system are also relevant to the process window. Varying these parameters can, therefore, be used to find RET defects. One method of achieving this is to take an image obtained using an inspection under a first set of conditions (i.e., a first set of sigma, NA and defocus), then take an image of the same reticle under a second set of conditions (i.e., varying one or more of the NA, sigma and defocus), and compare the resulting images. Such a method can be implemented, using an apparatus such as that shown in FIG. 13, simply by storing data taken from a first inspection of a reticle under a first set of conditions, varying parameters such as sigma, NA and/or defocus on the apparatus, and then re-inspecting the same reticle with the new parameter settings in place. The images are aligned prior to comparison. The stored data could be taken from inspection of an entire reticle (and stored on an optical disk or other media having suitable storage space), or could be taken across just a portion of the reticle (such as one or more swaths). If only a portion of the reticle inspection data is stored, storage might be appropriately handled in a memory buffer or the like. In some embodiments, the stored data may represent a "reference reticle field," or an aerial image of the reticle that would be produced at the best known process conditions, which may be stored such that it can be later used for transient repeating defect detection and/or non-transient defect detection.

In another embodiment, stored data could be taken from inspection of an entire die or just a portion of the die. In one such embodiment, the die or the portion of the die may correspond to a design pattern that is formed on the wafer using a reference member value of a set of lithographic values, which in some embodiments may be the best known conditions. In this manner, the stored data may represent a "reference die." In alternative embodiments, the stored data may be a simulated image. For example, the simulated image may be an image that would be printed on the wafer at the reference member value. In one embodiment, the simulated image may be generated from reticle design data. The reticle design data may be altered based on the reference member value to generate a simulated aerial image of the reticle. In a different embodiment, the simulated image may be generated from an aerial image of the reticle that is acquired by reticle inspection. The simulated aerial image or the acquired aerial image may be altered using a resist model to generate an image of the reticle that would be printed on the wafer at the reference member value.

The stored data may be compared to other die or portions of die on the wafer to determine a presence of defects on the wafer. In some embodiments, the die that are compared to the stored data may be printed at different conditions (i.e., not the reference member value). As such, the stored data may be used to determine a presence of transient repeating defects in the die or the portions of the die on the wafer. Alternatively, the die that are compared to the stored data may be printed at the same conditions as the stored data (i.e., the reference member value). Therefore, the stored data may be used to determine a presence of non-transient defects in the die or the portions of the die on the wafer.

As shown in FIG. 13, the system may include a number of other components including, but not limited to, homogenizer 1306, aperture 1307, condenser lens 1308, stage 1309, objective lens 1310, aperture 1311, lens 1312, beamsplitter 1313, and processor or computer 1314. The components may be configured as described in more detail in a commonly assigned copending application by Stokowski et al. having U.S. Ser. No. 10/679,617 filed Oct. 6, 2003. These components may be altered to provide varying parameters such as sigma, NA, the type of illumination, and the shape of the beam. For example, aperture 1307 may be altered to change sigma, the NA, the type of illumination, and the shape of the beam.

Figure 14A:
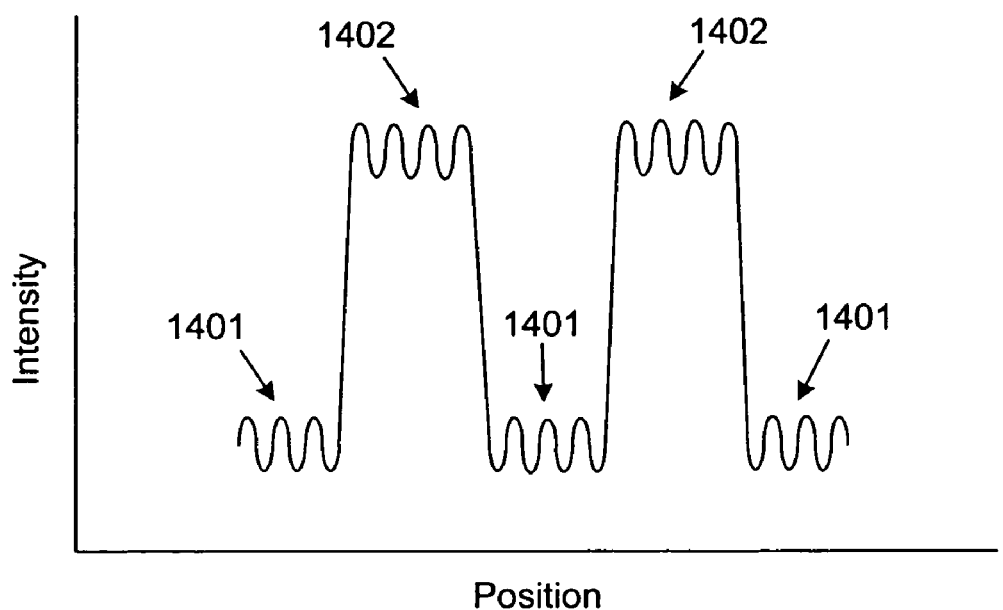
FIGS. 14A and 14B illustrate a method of processing detected signals in accordance with an embodiment of the invention.
Figure 14B:
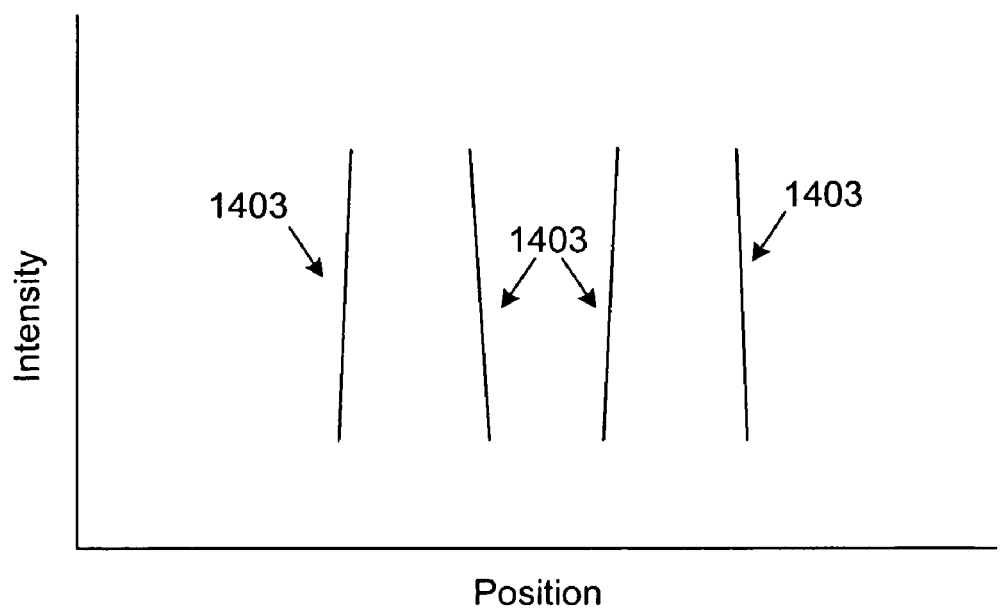

In a preferred embodiment, rather than directly comparing raw data from each detector (and/or from a rendered database), it may desirable to preprocess the data prior to comparison. One such preprocessing technique is illustrated in FIGS. 14A and 14B. FIG. 14A shows the intensity profile of light transmitted through a reticle. The areas of very low intensity 1401 may correspond to opaque regions (like chrome), and the regions of high intensity 1402 may correspond to transparent regions (like quartz). In the method of FIG. 14B, intensity data across the image is filtered (using a bandpass filter, for example) to remove all but the midrange intensity values 1403. These midrange values are associated with the edges of lines or other features printed using the reticle. Thus, errors associated with these values tend to be significant, and may relate to CD variation or other problems caused by RET defects. By contrast, the high and low range intensity values are often associated with lithographically insignificant variations. If one were to compare the total signals, including the high and/or low range intensity values for images taken by different detectors (or under different conditions, such as varied sigma or NA), the resulting comparison would tend to flag false defects because of the variations in these high and low intensity values. Thus, by removing the high and low intensity values before comparison, false defects are not flagged. Of course, this is only one example of a suitable preprocessing technique, and others could be envisioned. For example, a Gaussian filter could be applied to the signal. Or the signal could be differentiated one or more times, and those regions having first and second derivatives within appropriate ranges of values could be saved while others could be discarded. This technique could be used in conjunction with the example shown in FIG. 13, or could be used in connection with the DRC comparisons described herein.

In another preferred embodiment, the data taken from inspection by any method described herein (e.g., inspection using aerial images, inspection of images printed on a wafer, inspection of simulated images in accordance with DRC techniques, etc.) may be used to flag regions of a reticle or wafer for review. The coordinates for such review could be stored by the inspection apparatus and passed to a review tool (or performed on a review tool integrated into the inspection apparatus). In one preferred embodiment, the review tool is an aerial image review tool of the type commercially available from Carl Zeiss, Inc., Germany. Potential RET defect locations on a reticle are identified, and the coordinates passed to the Zeiss tool. Each such potential defect (or a sample statistically selected from a group of such defects) is then reviewed at varying levels of defocus (or other optical conditions, such as sigma or NA) to further study the possible defect and its potential significance.

If multiple similar RET defects are found during an inspection, they could be binned according to any desired method. In a preferred embodiment, these defects are binned by the appearance of the region immediately surrounding the defect. It has been discovered by the inventors that RET defects tend to be associated with the immediately surrounding pattern, and binning them by their surrounding pattern can both facilitate determination of the root cause of such defects, as well as avoid time consuming repetitive review of substantially identical defects associated with substantially identical regions.

It is to be noted that the above methods that use aerial images may also be performed in a similar manner using simulated images (e.g., images acquired using DRC techniques or ORC techniques).

The process window qualification (PWQ) methods and systems described above have proven to be useful and valuable tools and techniques for detecting defects in reticle design patterns. However, these methods and systems tend to detect a relatively large number of potential defects. As described above, the goal of PWQ is to detect and prioritize those defects that are caused by design or reticle limitations coupled with process window modulations. The excess defects that are detected increase the difficulty of identifying the most critical process window limiting defects and prioritizing the defects for review and/or possible repair. Additional methods and systems described herein provide an enhancement to the PWQ concept to provide increased signal-to-noise ratios for detecting process window limiting pattern errors. In addition, since the methods and systems described further herein are based on and utilize the process window concept, the methods and systems described further herein may be referred to as "Process Window Based" methods and systems. For example, the methods and systems described herein can be used for prioritization of a systematic repeater defect population. Therefore, such methods and systems may be referred to as "Process Window Based Prioritization" methods and systems.

In one embodiment, a computer-implemented method for detecting defects in a reticle design pattern includes acquiring images of a field in the reticle design pattern. The images illustrate how the field will be printed on a wafer at different values of one or more parameters of a wafer printing process. In one embodiment, the images of the field include images of the reticle design pattern printed on a wafer using the wafer printing process. Such images may be acquired as described above, for example, by printing the reticle design pattern on a wafer at the different values of the one or more parameters of the wafer printing process and imaging the wafer after the wafer printing process is completed. Imaging the wafer may be performed by a system such as that described further below. Alternatively, the images of the field may include aerial images of the reticle design pattern that is printed on a reticle. Such images may be acquired as described above, for example, using a system such as that shown in FIG. 13 as described further herein.

In another alternative, the images of the field may include simulated images. In this manner, the PWQ methods and systems described herein may be configured as virtual PWQ (vPWQ) methods and system. For example, simulated images may be generated by first simulating how the reticle design pattern will be printed on a reticle using a reticle manufacturing process. These simulated images may be used to simulate how the reticle design pattern printed on the reticle will be printed on a wafer using a wafer printing process. Like the methods described above, these simulated images may also be generated for different values of one or more parameters of the wafer printing process. The simulated images may be generated using a system as described further below. In addition, methods and systems for generating such simulated images are illustrated in U.S. patent application Ser. No. 11/048,630 entitled "Computer-Implemented Methods for Detecting Defects in Reticle Design Data" filed Jan. 31, 2005, which is incorporated by reference as if fully set forth herein.

The method also includes detecting defects in the field based on a comparison of two or more of the images corresponding to two or more of the different values. For instance, one field that is acquired for at least one modulated value of at least one of the parameter(s) of the wafer printing process may be compared to a reference field. The reference field corresponds to either the best known values for the one or more parameters being modulated or some predetermined values for the one or more parameters. Potential defects are identified as differences between the compared field images.

Figure 15:
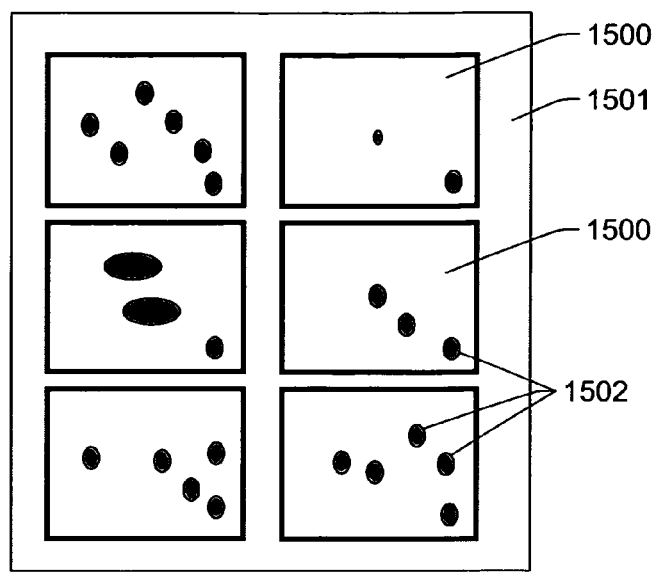
FIG. 15 is a schematic diagram illustrating a top view of a defect map of a field in a reticle design pattern that includes multiple identically designed die.

FIG. 15 illustrates one example of multiple die 1500 that may be included within field 1501 in the reticle design pattern. Defects 1502 are detected in the multiple die by comparing the field with another field as described above. Although the defects are shown in FIG. 15 as having various shapes, sizes, and locations, these defects are illustrated only as examples to promote understanding of the methods described herein. It is to be understood that the defects may have any size, shape, and location. Although the field is shown in FIG. 15 as having a 2×3 arrangement of die, it is to be understood that the field may have any arrangement or layout of multiple die. In addition, although the field is shown as having 6 die, it is to be understood that the methods that are further described herein may be performed with a field having at least a first die and a second die (i.e., two or more die). In the field illustrated in FIG. 15, all 6 die are similarly configured. In other words, all 6 die are designed to have the same reticle design pattern.

When the methods described herein are used to detect defects in a reticle design pattern of a multi-die reticle, the methods include determining if individual defects located in the first die have substantially the same within die position as individual defects located in the second die. Therefore, unlike the die comparison described above for conventional reticle inspection, which involves identifying defects that are unique to each die, this step involves identifying defects that are "common" to multiple die. In one such embodiment, the determining step may include comparing an image of one die to an image of another die. In such an embodiment, the die images may be translated from within field coordinates or other positional information to within die coordinates or positional information. The images may then be aligned using the within die coordinates. In this manner, the image of one die at one position can be compared to the image of another die at the same within die position.

In another embodiment, determining if individual defects are located in multiple die at substantially the same within die position may include "die stacking." For the sake of convenience, this determining step is referred to herein as "die stacking," but it is to be understood that the determining step may be performed as described above without actually stacking the die. Die stacking may be performed in a manner similar to that described above for field stacking. In other words, the image data for two or more die can be overlaid such that differences or similarities between the die can be identified.

Figure 16:
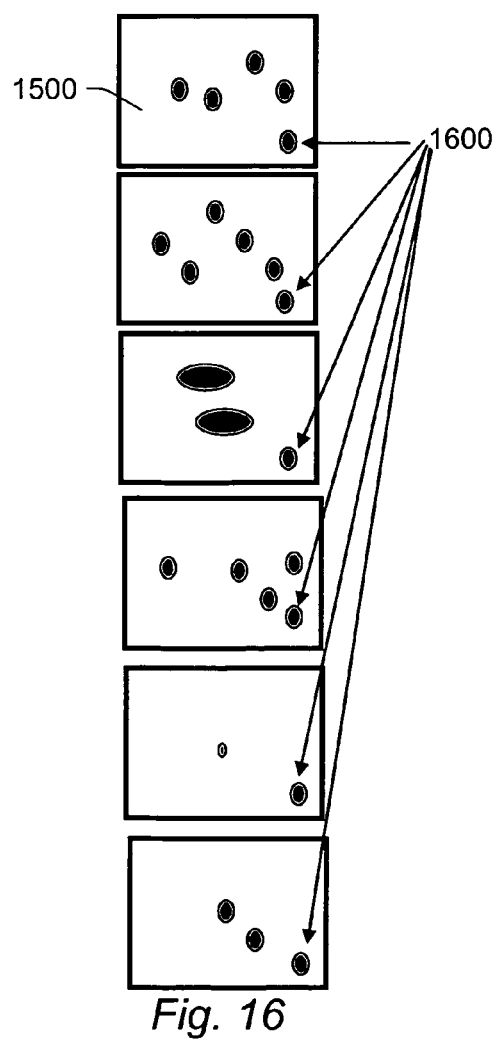
FIG. 16 is a schematic diagram illustrating; a top view of multiple die in a field in which individual defects are located in the multiple die at substantially the same within die position and have a characteristic that is substantially the same.
Figure 17:
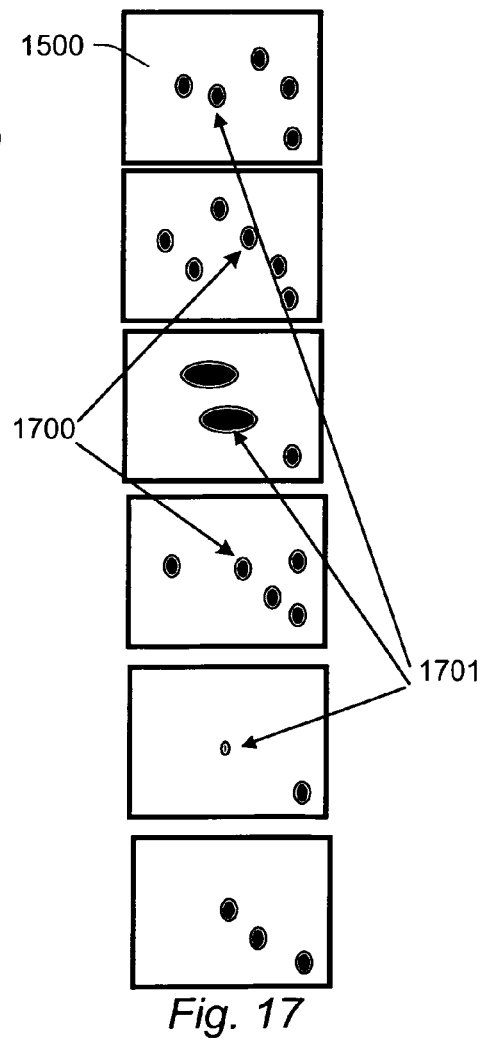
FIG. 17 is a schematic diagram illustrating a top view of multiple die in a field in which first individual defects are located at substantially the same within die position in fewer than all of the multiple die and have a characteristic that is substantially the same and in which second individual defects are located at substantially the same within die position in fewer than all of the multiple die but have a characteristic that is different.

Although the die stacking step is described above with respect to just two die, it is to be understood that the die stacking step may be performed with all of the die in the field. For example, as shown in FIG. 16, all six of the die in the field may be used for die stacking. Die stacking will identify defects 1600, which are located in all of the die at the same within die position. However, some defects may not appear in all of the die. For example, as shown in FIG. 17, defects 1700 appear in multiple die, but fewer than all of the die, at the same within die location. In addition, defects 1701 appear in multiple die, but fewer than all of the die, at the same within die location.

Defects having the exact same intra-die coordinates can be designated as potentially important, process window limiting defects. However, the coordinates of the defects determined or reported by the optical or other system used to acquire the field images may have some relatively small errors. Therefore, an adjustable tolerance may be used to identify the coordinates of a within die position that can be considered to be substantially the same. In one such embodiment, the substantially the same within die position may include a range of within die positions defined by a single within die position and a predetermined tolerance for acceptable positional variance. The predetermined tolerance may vary depending on a number of variables of the method such as the accuracy of the optical system used to acquire the images, the accuracy of the simulation engine used to acquire the images, expected or possible variations in the reticle or wafer that would lead to positional variance in the defects, or any other such variable of the method.

In another example, it may be desirable to categorize multiple individual defects as a single design pattern defect. For example, a design pattern defect may appear in the die as multiple spatially separated individual defects such as multiple micro bridges 2000 illustrated in FIG. 20, which indicate a distributed failure along reticle design pattern features 1801 and 1802. However, since each of these defects are caused by the same design pattern marginality, it would be disadvantageous to identify them as different design pattern defects. Therefore, the predetermined tolerance for positional variance may be varied depending on factors such as the number of defects that can be expected, the types of defects that may be present in the reticle design pattern, characteristics of the design pattern such as size, shape, symmetry in the design pattern in either Cartesian or Polar coordinate systems, etc.

Figure 18:
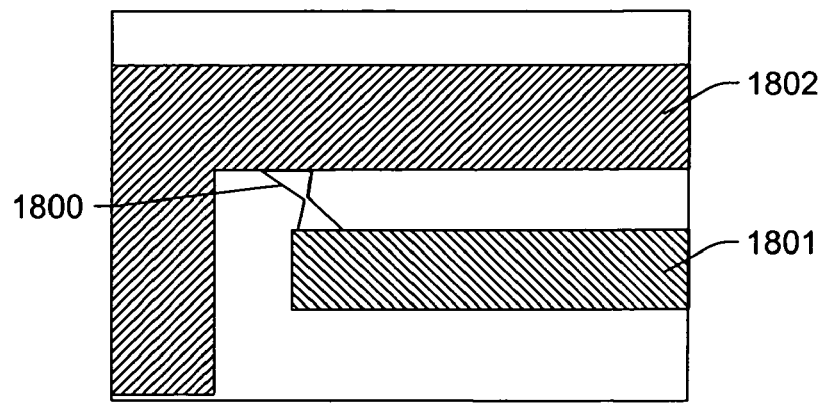
FIG. 18 is a schematic diagram illustrating a top view of one example of a defect that may occur in a field of a reticle design pattern at small modulation of values of one or more parameters of a wafer printing process.
Figure 19:
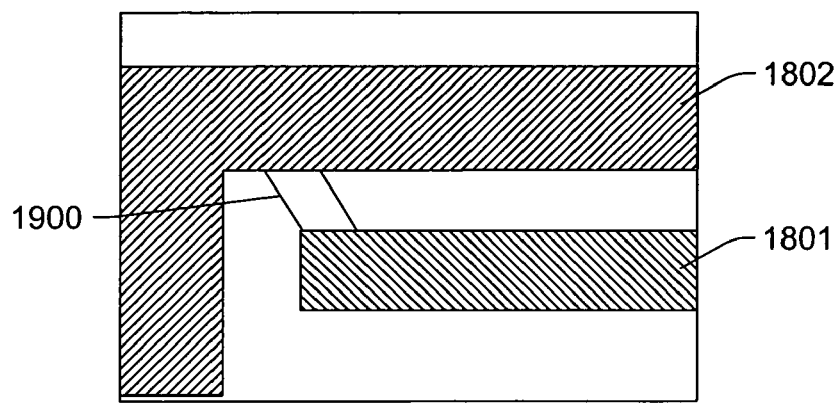
FIGS. 19 and 20 are schematic diagrams illustrating top views of different examples of defects that may occur in a field or a reticle design pattern at large modulation of values of one or more parameters of a wafer printing process.

This adjustable tolerance concept may also be applied to field stacking. For example, as shown in FIG. 18, at small modulation, relatively small micro bridge 1800 between features 1801 and 1802 of the reticle design pattern may be detected in a field image, which may indicate the beginning (or the extent) of a failure of the reticle design pattern. As the modulation increases, the reticle design pattern defect may manifest in different ways. For example, as shown in FIG. 19, in one example of large modulation, the small micro bridge that was apparent at small modulation, now appears as large full bridge 1900, which indicates a localized failure in the reticle design pattern. Since the large full bridge appears in the image illustrated in FIG. 19 at substantially the same within field position as the relatively small micro bridge shown in the image illustrated in FIG. 18, the repeating process window defect can be detected with a relatively tight tolerance for positional variance.

Figure 20:
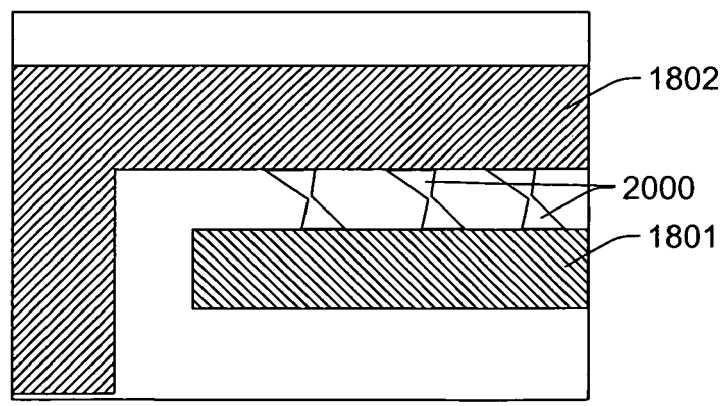

However, as shown in FIG. 20, in a different example of how the small modulation defect may manifest at large modulation, the small micro bridge now appears as multiple micro bridges 2000 between features 1801 and 1802, indicating a distributed failure along these features of the reticle design data. As further shown in FIG. 20, the micro bridges are not located at the same exact within field position as the small micro bridge of FIG. 18. Therefore, even though the defects shown in FIGS. 18 and 20 may be caused by the same reticle design pattern marginality, the defects shown in FIGS. 18 and 20 will not be detected as repeating, process window limiting defects if a tight tolerance for positional variance is used for field stacking. In contrast, if a relaxed tolerance is used for field stacking, the defects shown in FIGS. 18 and 20 will be identified as repeating defects. In this manner, the tolerance may be adjusted based on the types of defects that are expected. In another manner, the tolerance may be adjusted in real time or during the field stacking step. For example, if no repeating defects are found using a tight tolerance for positional variance, the tolerance may be relaxed to determine if there are defects that are relatively "nearby" that may qualify as repeating defects.

Obviously, the defects shown in FIGS. 19 and 20 will have different impacts on the process window that can be used with the reticle design pattern. In this manner, the defects shown in FIGS. 19 and 20 can be assigned different priorities as described further herein. For example, the defects may be assigned different priorities based on the characteristics of the defects. In particular, the defect shown in FIG. 19 can be assigned a higher priority than the defects shown in FIG. 20 since the defect shown in FIG. 19 is larger in size than the defects shown in FIG. 20. In another example, the defect shown in FIG. 19 can be assigned a higher priority than the defects shown in FIG. 20 based on the different shapes of the defects. In other words, the shape of the defect shown in FIG. 19 is indicative of a full bridge between the features and, therefore, may be designated a more important process window limiting defect than the defects shown in FIGS. 20. Different prioritizations can be assigned to the defects by using either preset rules (e.g., if the x and y positions of two defects are not different by certain distance, then two defects are the same) or algorithms (e.g., for analysis of defects that cannot be easily performed using rules such as identifying distributed defects and localized defects and assigning different priorities to the distributed defects and the localized defects, determining the severity of different defects (e.g., by examining characteristics of the defects such as size in the x and/or y dimensions) and assigning different priorities to defects having different severities, etc.). The rules and the algorithms may have any suitable configuration known in the art.

In some embodiments, a sensitivity of the die stacking in a first region of the first and second die may be different than a sensitivity of the die stacking in a second region of the first and second die. In this manner, the sensitivity of determining whether or not individual defects are located at substantially the same within die position may vary from region to region with the die. For example, a region of the die corresponding to device structures may have an increased sensitivity for determining if the individual defects are located at substantially the same within die position while a region of the die corresponding to test structures may have a lower sensitivity for determining if the individual defects are located at substantially the same within die position. The sensitivity may be altered, for example, by altering the predetermined tolerance for acceptable positional variance from region-to-region within the die.

Determining if individual defects are located at substantially the same position within multiple die of a reticle field improves the signal-to-noise of the method by averaging over all of the nominally identical die in a field. For instance, defects that do not appear at substantially the same within die position in multiple die may be designated as random defects or other defects not attributable to marginalities in the reticle design pattern. In some embodiments, the method may include filtering the individual defects based on results of the determining step. In this manner, these non-process window limiting defects may be eliminated from the data that is used to identify and prioritize process window limiting defects in the reticle design data.

In some embodiments, the method may also include determining if the individual defects that are located in the first and second die at substantially the same within die position have a characteristic that is substantially the same. The characteristics that are compared for defects appearing at substantially the same within die position may include, but are not limited to, size, shape, structure in the reticle design data affected by the defect, or any other measurable characteristic of the defects. For example, as shown in FIG. 16, defects 1600 would be determined as having the same basic size and shape. In addition, as shown in FIG. 17, defects 1700 would be determined as having the same basic size and shape. In contrast, defects 1701 would be determined as having different sizes and different shapes.

However, using images of the reticle design pattern printed on a wafer, defects do not always print the exact same way due to, for example, small differences in local exposure conditions (such as wafer flatness and local topography, film thickness variation, lens aberrations, illumination uniformity, etc.). Defects are also not always imaged exactly the same way by optical systems including those described herein due to minor variations in the optical systems such as, but not limited to, lens aberrations, imbalance between elements in the detector, and illumination non-uniformity, both spatially and temporally (fluctuations over time). Therefore, defects that are actually the same type of defect and located at the same within die position may not be identified as such due to variations in the local exposure conditions and variations in the image acquisition system.

As such, like the determination of whether or not defects in different die are located at substantially the same within die position, determining if the individual defects have one or more characteristics that are substantially the same may also be configured to account for variance in the characteristic(s). In one such embodiment, a characteristic qualifies as being substantially the same if a value of the characteristic is within a range of values for the characteristic. The range of values can be defined by a single value for the characteristic and a predetermined tolerance for acceptable characteristic variance.

The methods described herein may also be modified to account for other types of variability or inaccuracy. For example, a repeating defect in one die may be "covered" or obscured by a larger or more pronounced random defect. To account for such overlapping defects, in one embodiment, if individual defects have substantially the same within die position but one or more different characteristics such as size, the method may include determining if one of these individual defects is a random defect obscuring a defect in the reticle design pattern. In one example, a random defect may be identified by comparing one or more characteristics of the potentially random defect to a range of expected characteristics for the process window limiting defects. For instance, a random defect such as a defect caused by a local variation in the topography of the wafer may be relatively large compared to the expected size of the process window limiting defects. In another example, a random defect may be qualified as such based on information about the potentially random defect in the acquired images. For instance, a random defect may alter the polarization of the light in the image differently than design pattern defects do. In this manner, the polarization of the light reflected from different defects or any other information obtained by the system used to acquire the images may be used to identify those defects that may be random defects.

In this manner, adjustable tolerances can be applied to determine if defects are "identical" despite small differences in size, appearance, and other attributes. A sliding scale or priorities can be applied based on a) the number of die in which the defect occurs at substantially the same coordinates and with substantially the same attributes, b) the number of die in which the defect might have appeared but may have been covered by larger random defects, and c) the number of die in which a defect does appear at the same or nearly the same coordinates but with different attributes. A weighting factor can be applied based on the relative difference between the expected coordinates and those of the detected defect and between the expected attributes and those of the detected defect.

Defects that appear in substantially the same location in each of the multiple die with substantially the same characteristics or attributes such as, but not limited to, size, shape, structure affected, etc. can be determined to be the most critical defects in the field since these defects are clearly design induced repeating defects (or "systematic defects").

Therefore, in one embodiment, methods described herein may also include assigning a priority to the individual defects based on results of the determining step. For instance, a higher priority may be assigned to the individual defects that are located in multiple die at substantially the same within die position than the individual defects that are not located in the multiple die at substantially the same within die position. In another example, different priorities can be assigned to the individual defects based on how many die the nominally identical defects are found.

In addition, priorities can be assigned to individual defects based on a number of factors that reflect how "identical" the individual defects located at substantially the same within die position appear to be. In one such embodiment, a higher priority can be assigned to the individual defects that are located in multiple die at substantially the same within die position and have one or more characteristics that are substantially the same than a priority assigned to the individual defects that are located in the multiple die at substantially the same within die position and exhibit differences in the one or more characteristics.

In one example based on the defects shown in FIGS. 16 and 17, defects 1600 would be assigned the highest priority since these defects appear in all of the die at the same within die position and have the same basic size and shape. Defects 1700 may be assigned a lower priority since these defects repeat in multiple, but not all, die, at the same within die position and have the same basic size and shape. In contrast, defects 1701 may be assigned the lowest priority of the three different defects since these defects appear in multiple, but not all, die at the same within die position and have different sizes and/or shapes.

By applying die stacking or a similar comparison, a composite priority can also or alternatively be assigned to each defect that more accurately reflects its importance in defining the process window limits for the reticle design pattern. For example, the method may include assigning a composite priority to the individual defects based on results of the determining step in combination with the different values corresponding to the images of the field. In particular, the die stacking step described above will often be performed for multiple field images, and the different field images may be acquired for different values of the one or more parameters of the wafer printing process. In this manner, the priorities that are assigned to the defects within the multiple die field may be based not only on whether or not the individual defects are located at substantially the same within die position and have one or more characteristics that are substantially the same, but also on the modulation level of the multi-die field. In one such example, individual defects located at substantially the same within die position in a multi-die field having a relatively low level of modulation may be assigned a higher priority than individual defects having substantially the same within die position in a multi-die field having a relatively high level of modulation since the defects appearing at the low level of modulation may limit the usable process window for the reticle design pattern more than the other defects. The methods described herein, therefore, not only increase the signal-to-noise ratio for defect detection in multi-die reticles but also aid in the prioritization of the most repetitive process window limiting defects for review and/or correction of the reticle design pattern.

A composite priority can also be assigned to each defect that more accurately reflects its importance with respect to the design of the device. For example, the method may include assigning a composite priority to the individual defects based on results of the determining step in combination with context or background of the individual defects. In particular, the die often include different types of design structures such as device structures and test structures that when defective have different impacts on yield. In this manner, the priorities that are assigned to the defects within the multiple die field may be based not only on whether or not the individual defects are located at substantially the same within die position and have one or more characteristics that are substantially the same, but also on the context of the individual defects within the device design. In one such example, individual defects located at substantially the same within die position and within a critical portion of the device design may be assigned a higher priority than individual defects located at substantially the same within die position and within a non-critical portion of the device design since the defects appearing in the critical portion of the device design may have a greater impact on yield than other defects. In such embodiments, composite priorities may also be assigned based on the modulation level of the multi-die field as described further above. The methods described herein, therefore, not only increase the signal-to-noise ratio for defect detection in multi-die reticles but also aid in the prioritization of the most repetitive yield limiting defects for review and/or correction of the reticle design pattern.

In other words, the methods described herein can use background based or pattern based binning to further modify the prioritization and "trim" the review defect population using the feature layout and/or neighborhood information associated with the individual defects. Examples of methods and systems for background or pattern based binning and/or for determining the position of an individual defect in design data space that can be used in the methods described herein are illustrated in U.S. patent application Ser. Nos. 11/005,658 entitled "Computer-Implemented Methods for Detecting and/or Sorting Defects in a Design Pattern of a Reticle" filed Dec. 7, 2004 by Wu et al., 60/738,290 entitled "Methods and Systems for Utilizing Design Data in Combination with Inspection Data" filed Nov. 18, 2005 by Kulkarni et al., and Ser. No. 11/300,172 entitled "Methods and Systems for Binning Defects Detected on a Wafer" filed Dec. 14, 2005 by Lin et al., which are incorporated by reference as if fully set forth herein. The method embodiments described herein may include any step(s) of any of the method(s) described in these patent applications.

In some embodiments, the methods described above may include selecting the multiple die within the field that are used for die stacking based on locations of the multiple die within the field. For example, multi-die reticles sometimes exhibit increased defectivity on one side of the exposure field compared with the other side. In one particular example, as shown in FIG. 21, dies 2100 that are located on the right side of the reticle field may show a larger population of defects than dies 2101 that are located on the left side of the reticle field. Such localized defectivity may be caused by an interaction between the marginalities within the reticle design pattern and the optical non-idealities in the lens field. In such cases, the die based prioritization of the individual defects may be customizable to allow a user to select only the pertinent die from the entire n×n die array within a reticle. For instance, in the example shown in FIG. 21, the user may select dies 2100 located on the right side of the reticle field for die stacking and defect prioritization. Alternatively, the selection of the dies for die stacking may be performed by the computer-implemented methods and systems described herein based on the number of defects detected in each die by the field comparison step described above and/or known non-idealities in the lens field. Selecting the die used in the die stacking step will assist in the prevention of masking of such interaction defects by the all-die repeating defect population.

In another embodiment, the methods described herein may include determining the reticle field distribution with the field tilt of an exposure tool (e.g., a scanner) mapped to the data collected for the reticle. In addition, a known field tilt may be subtracted from the data collected for an unknown reticle. The results of these steps may be used to select the multiple die within the field that are used for die stacking and defect prioritization based on the locations of the multiple die within the field, which may be performed as described above. Selecting the die used in the die stacking step in this manner will assist in preventing masking of defects caused by interactions between the marginalities within the reticle design pattern and the field tilt by the all-repeating defect population.

In additional embodiments, the field in the reticle design pattern may include die for different devices. For example, multi-device or shuttle reticles may sometimes be utilized in foundry fabs. In one particular example, as shown in FIG. 22, the reticle field may include four different die 2200, 2201, 2202, and 2203, each of which contains the reticle design pattern for a different device. Although the reticle field is illustrated in FIG. 22 as having four different die, each for a different device, it is to be understood that the reticle field may include any number of die. In addition, more than one of the die may contain the reticle design pattern for the same device. For example, the reticle design pattern in die 2201 may be replaced with the reticle design pattern of die 2203 such that the reticle field includes more than one die for the same device.

In one such embodiment, the method may include selecting the multiple die within the field for the die stacking step based on the different devices associated with the die. The above described customizable die selecting option can also be configured to allow the user to pick any number of die from the total array in the field to be used for the die stacking. For instance, in the example shown in FIG. 22, if the device of die 2203 is being analyzed by the computer-implemented methods and systems described herein, the user would select die 2203 for die stacking and prioritization of the defects. In addition, the die may be selected for die stacking based on the device associated with the die by the computer-implemented methods and systems described herein. Selecting the die used for die stacking in this manner will allow the acquired images to be analyzed for each specific device in a completely separate manner.

In further embodiments, a portion of the die used in the die stacking step may be selected in a similar manner. For example, if the die includes multiple different types of regions such as device regions and test regions, die stacking may be performed in the device regions but not the test regions. Alternatively, different types of regions within the die may be inspected with different sensitivities as described further above. In addition, the individual defects and their assigned priorities may be assigned a region identifier, which indicates the type of region in which the individual defects are located. Such region-based information may be utilized in a number of different ways. For example, the defectivity of the individual regions may be separately determined. In addition, individual regions can be assigned a priority based on how defective the individual regions are. Therefore, individual regions within a die can be identified as more process window limiting or less process window limiting.

In some embodiments, the die stacking methods described above may be performed before, after, or concurrently with field stacking, which may be performed as shown in FIG. 10. Some PWQ defects may occur in only one die of a multi-die reticle due to minor manufacturing differences between die in the reticle. Therefore, both stacked and "unstacked" analyses may be performed either serially or in parallel, and priorities may be assigned based on a combination of the field and die stacking analyses. In addition, the die stacking methods described above may include any other step(s) described herein.

FIG. 23 illustrates one embodiment of a system that is configured to detect defects in a reticle design pattern. As shown in FIG. 23, the system includes optical subsystem 2300. Optical subsystem 2300 is configured to acquire images of a field in the reticle design pattern. The images illustrate how the field will be printed on a wafer at different values of one or more parameters of a wafer printing process. The field includes a first die and a second die. In addition, the field may include two or more die.

As shown in FIG. 23, the optical subsystem includes light source 2301. The light source may include any suitable light source known in the art. In addition, the light source may be configured to generate monochromatic light, near monochromatic light, polychromatic light, or broadband light. Light generated by light source 2301 is directed by optical component 2302 to lens 2303. In one example, optical component 2302 may be a beam splitter. However, optical lo component 2302 may include any suitable optical component known in the art. Lens 2303 may be a refractive lens such as an objective lens or any other suitable refractive component known in the art. Although lens 2303 is shown in FIG. 23 as a single optical component, it is to be understood that multiple lenses may be used in place of lens 2303. In addition, lens 2303 may be replaced with a reflective optical component such as a focusing mirror.

Light focused by lens 2303 is directed to wafer 2304, which is disposed on stage 2305. As shown in FIG. 23, light may be directed from the lens to the wafer at a normal angle of incidence. However, the light may be directed to the wafer at an oblique angle of incidence. Wafer 2304 is a wafer on which the reticle design pattern is printed using the wafer printing process. In other words, wafer 2304 includes multiple reticle fields printed at different values of one or more parameters of the wafer printing process. The reticle fields may be printed on the wafer as described further above.

Light reflected from wafer 2304 is collected by lens 2303 and passes through optical component 2302. Light passed through optical component 2302 is directed to detector 2306. Detector 2306 is preferably a detector capable of forming an image of the reticle fields printed on the wafer. The detector may include any such detector known in the art such as, but not limited to, a charge coupled device (CCD). As shown in FIG. 23, the optical subsystem is configured as a bright field imaging optical subsystem. However, the optical subsystem may have any other optical configuration known in the art that is suitable for acquiring images of the reticle field in the reticle design pattern.

In some embodiments, the optical subsystem shown in FIG. 23 may be configured to acquire images of the wafer at different defocus settings. For example, in one such embodiment, the optical subsystem may include two or more detectors (not shown), each of which is arranged at a different elevation with respect to the substrate. In this manner, the arrangement of the detectors creates a pseudo defocus effect, and the optical subsystem can use constant settings to image the reticle fields printed on the wafer. In some such embodiments, the multiple detectors of the optical subsystem shown in FIG. 23 may be further configured as described above with respect to the detectors of FIG. 13.

In an alternative embodiment, stage 2305 shown in FIG. 23 may be configured such that a position of wafer 2304 with respect to the optical subsystem can be altered. In particular, the stage may be configured to move the wafer toward and away from the optical subsystem. In this manner, the wafer may be located at different elevations with respect to the optical subsystem while different images of the reticle fields printed on the wafer are acquired. As such, the different positions of the wafer with respect to the optical subsystem simulates scanner defocus for process window mapping. In a different embodiment, the optical subsystem shown in FIG. 23 may include only one detector (e.g., detector 2306), and the position of the detector may be altered to change the distance between the detector and the wafer thereby effectively changing the focus setting of the optical subsystem. In this manner, the position of the detector may be altered between acquiring different images of the wafer or between different scans of the wafer such that different images of the reticle fields printed on the wafer are acquired at different focus settings. In addition, the focus setting of the optical subsystem shown in FIG. 23 may be altered in any other suitable manner known in the art such that images of the reticle fields printed on the wafer can be acquired at different defocus settings.

As further shown in FIG. 23, the system includes processor 2307, which is coupled to optical subsystem 2300. For example, processor 2307 may be coupled to detector 2306 by transmission medium 2308. The transmission medium may include any suitable transmission medium known in the art and may include "wired" and/or "wireless" portions. In addition, processor 2307 may be coupled directly to detector 2306 by transmission medium 2308, or one or more components (not shown) such as an analog-to-digital converter may be interposed between the detector and the processor. Processor 2307 may be coupled to other components of the optical subsystem in a similar manner. The processor may include any suitable processor known in the art such as that included in an imaging computer.

In this manner, processor 2307 can acquire the images generated by detector 2306. Processor 2307 is configured to detect defects in the field based on a comparison of two or more of the images corresponding to two or more of the different values of the parameter(s) of the wafer printing process. The processor may detect the defects in the field as described further above (e.g., by field stacking). In addition, the processor is configured to determine if individual defects located in the first die have substantially the same within die position as individual defects located in the second die. The processor may be configured: to perform this determining step as described further above (e.g., by die stacking). The processor may also be configured to perform any other step(s) described herein such as assigning a priority and/or a composite priority to the individual defects. The processor may be further configured as described herein.

The optical subsystem shown in FIG. 23 is, therefore, configured to acquire the images of the field in the reticle design pattern by imaging a wafer on which the reticle design pattern is printed using the wafer printing process. In another embodiment, the optical subsystem shown in FIG. 23 may be replaced by an optical subsystem that is configured as an aerial imaging measurement system (AIMS) such as that shown in FIG. 13. The system shown in FIG. 23 may be further configured as described herein.

Figure 24:
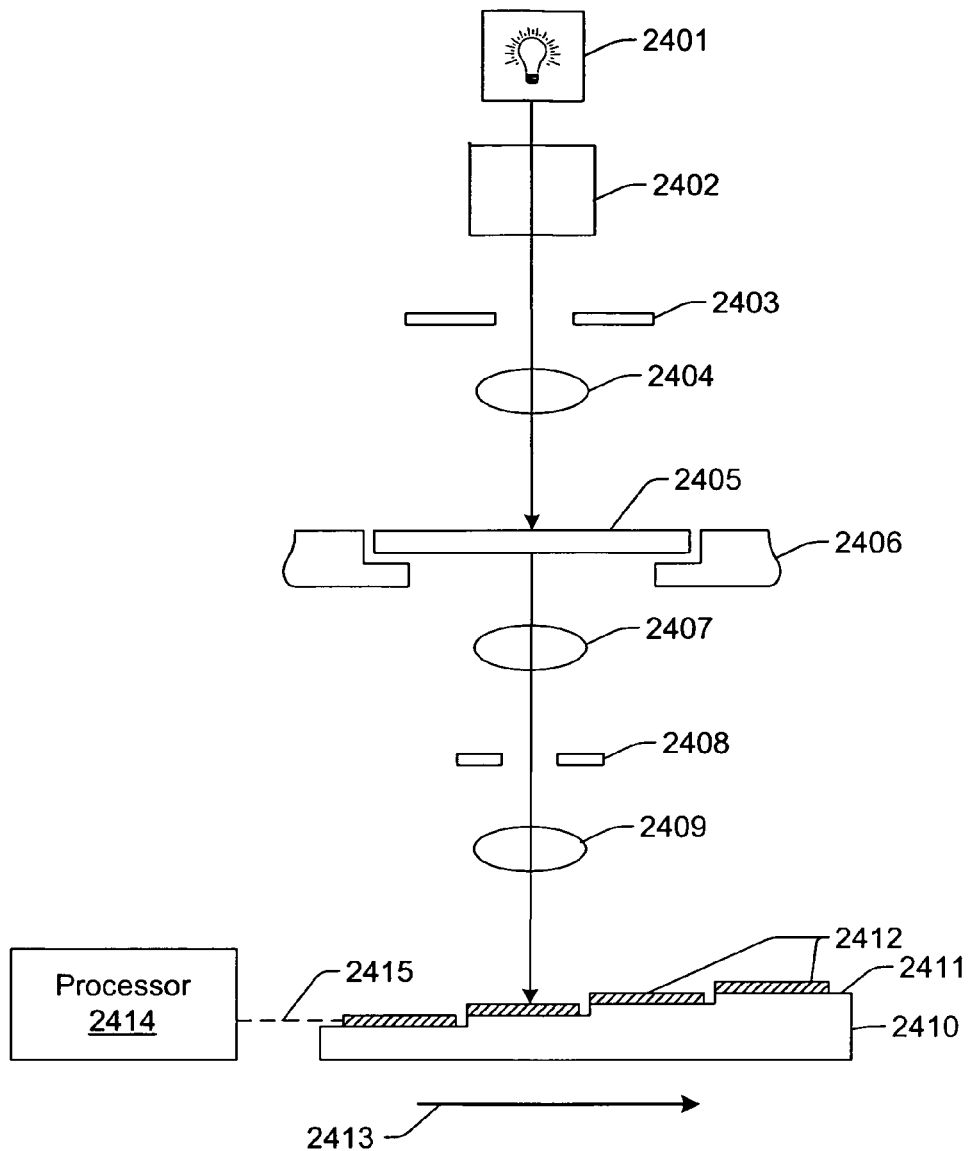

FIG. 24 illustrates another embodiment of a system that is configured to detect defects in a reticle design pattern. The system includes an optical subsystem configured to acquire images of a field in the reticle design pattern. The images illustrate how the field will be printed on a wafer at different values of one or more parameters of a wafer printing process. The field includes a first die and a second die. In addition, the field may include two or more die.

As shown in FIG. 24, the optical subsystem includes light source 2401. The light source may include any suitable light source known in the art. In addition, the light source may be selected to simulate the light that a reticle would be illumination with during a lithography process. For example, the light source may be configured to generate light having substantially similar characteristics (e.g., wavelength, polarization, intensity, etc.) as light generated by a light source of an exposure tool. Light generated by light source 2401 passes through homogenizer 2402, aperture 2403, and condenser lens 2404. Light exiting condenser lens 2404 illuminates reticle 2405. Homogenizer 2402, aperture 2403, and condenser lens 2404 may include any suitable such optical components known in the art. In addition, homogenizer 2402, aperture 2403, and condenser lens 2404 may be selected such that the light that illuminates reticle 2405 has substantially similar characteristics as light that will illuminate the reticle in an exposure tool. Reticle 2405 may be supported on stage 2406 during illumination of the reticle. Stage 2406 may include any suitable mechanical or robotic assembly known in the art.

The optical subsystem also includes objective lens 2407 that is configured to collect light transmitted through reticle 2405. Light collected by objective lens 2407 passes through aperture 2408 and lens 2409. Objective lens 2407, aperture 2408, and lens 2409 may include any suitable such optical components known in the art. Light exiting lens 2409 is focused on wafer 2410. Objective lens 2407, aperture 2408, and lens 2409 may be configured to simulate the light that would be focused onto a wafer by an exposure tool using reticle 2405.

Wafer 2410 may include a bare silicon substrate or another suitable substrate having upper surface 2411. As shown in FIG. 24, the height of upper surface 2411 varies across the wafer. The variations in the height of upper surface 2411 may be formed by one or more masking and etching steps that are used to etch the wafer to varying degrees in different areas. Therefore, the wafer may include recesses having various depths. Although one dimension of wafer 2410 (e.g., the x dimension or the y dimension) is shown in FIG. 24 having a number of recesses formed along this dimension, it is to be understood that the wafer may include a number of recesses formed along both dimensions (i.e., the x and y dimensions) of the wafer. In this manner, the wafer may include a one-dimensional array of recesses or a two-dimensional array of recesses. Furthermore, although the upper surface of the wafer is shown in FIG. 24 as having three recesses with different depths (e.g., an upper surface having four different heights including the heights of the three recesses and the original upper surface of the wafer), it is to be understood that the wafer may have any suitable number of recesses known in the art.

The optical subsystem includes sensors coupled to a substrate and positioned at different heights with respect to reticle 2405 on which the reticle design pattern is formed. The sensors are configured to acquire the images. For example, sensors 2412 are coupled to wafer 2410. Sensors 2412 may include any suitable type of sensors such as CCD flash sensors or any other suitable photometric sensors known in the art. Sensors 2412 are preferably configured to detect the light exiting lens 2409 to form images of the light transmitted by the reticle. Therefore, the optical subsystem of the system shown in FIG. 24 is configured as an aerial imaging measurement system.

Sensors 2412 may be positioned on the upper surface of the wafer at the various heights. Therefore, as shown in FIG. 24, the sensors are positioned at different heights with respect to reticle 2405. As such, the sensors are arranged at different focal planes with respect to the reticle. In this manner, the sensors effectively simulate different levels of defocus at which an image of the reticle would be printed on a wafer. In particular, the recesses may be formed in the upper surface of the wafer such that each of the sensors is positioned at a focal plane that simulates one possible level of defocus of an exposure tool that will be used to expose a wafer using reticle 2405. For example, the recesses may have heights that differ from each other by about 0.1 µm. Therefore, the four recesses shown in FIG. 24, from left to right in the figure, may simulate defocus levels of −0.3 µm, −0.2 µm, −0.1 µm, and 0 µm. Obviously, these values of defocus are merely examples, and any selected levels of defocus may be simulated based on the exposure tool configuration by varying the height of each of the recesses. For example, the sensors may be positioned at positive levels of defocus, or some of the sensors may be positioned at positive levels of defocus while others are positioned at negative levels of defocus. In addition, the levels of defocus simulated by the different sensors may be selected to provide the user with information regarding RET defects and the appearance of such defects across the process window. Furthermore, the levels of defocus that are simulated by the sensors may be altered globally by altering the distance between the wafer and the optical components of the optical subsystem.

In addition, the wafer may include a relatively large number of recesses that can be used to simulate a relatively large number of defocus levels, and depending on the configuration of the exposure tool, only some of the sensors positioned in all of the recesses may be used to acquire images of any particular reticle. Therefore, the system shown in FIG. 24 may be used to acquire images of a field in a reticle design pattern regardless of which exposure tool the reticle will be used with.

Unlike some systems described herein, therefore, the optical subsystem shown in FIG. 24 may not be configured to alter the position of one or more optical components of the system or the distance between the wafer and the optical components of the system to simulate different levels of defocus. Instead, the optical subsystem is configured to acquire images of a field in the reticle design pattern that illustrate how the field will be printed on the wafer at different values of defocus of a wafer printing process by imaging the light transmitted through the reticle onto the different sensors. The light transmitted through the reticle may be imaged onto the different sensors by moving wafer 2410 (e.g., in a stepwise or scanning fashion) in a direction such as that shown by arrow 2413.

Since wafer 2410 includes more than one sensor, each of which is configured to simulate a different level of defocus, acquiring the images of the reticle using the sensors may be performed relatively quickly particularly compared to using a single sensor to acquire the images at the different levels of defocus, which requires that the sensor be allowed to "reset" (e.g., by allowing the current to drain) after each image at one level of defocus is acquired. In addition, the optical subsystem shown in FIG. 24 may be configured to alter other parameters (e.g., NA) of the system that are relevant to the process window as described further herein.

As further shown in FIG. 24, the system includes processor 2414, which is coupled to the optical subsystem. For example, processor 2414 may be coupled to each of sensors 2412 by a transmission medium (e.g., as shown schematically in FIG. 24 by transmission medium 2415). The transmission medium may be configured as described above. In addition, processor 2414 may be coupled directly to sensors 2412 by transmission media, or one or more components (not shown) such as an analog-to-digital converters may be interposed between each of the sensors lo and the processors. Processor 2414 may be coupled to other components of the optical subsystem in a similar manner. The processor may include any suitable processor known in the art such as that included in an imaging computer.

In this manner, processor 2414 can acquire the images generated by sensors 2412. Processor 2414 is configured to detect defects in the field based on a comparison of two or more of the images corresponding to two or more of the different values of the parameter(s) of the wafer printing process. For example, processor 2414 may be configured to detect defects in the field by comparing two or more of the images generated by two or more of the sensors corresponding to two or more of the different values of defocus. The processor may detect the defects in the field as described further above (e.g., by field stacking).

The processor is also configured to determine if individual defects located in the first die have substantially the same within die position as individual defects located in the second die. The processor may be configured to perform this determining step as described above (e.g., by die stacking). The processor may also be configured to perform any other step(s) described herein such as assigning a priority and/or a composite priority to the individual defects. The processor may be further configured as described herein. The system shown in FIG. 24 may be further configured as described herein.

Figure 25:
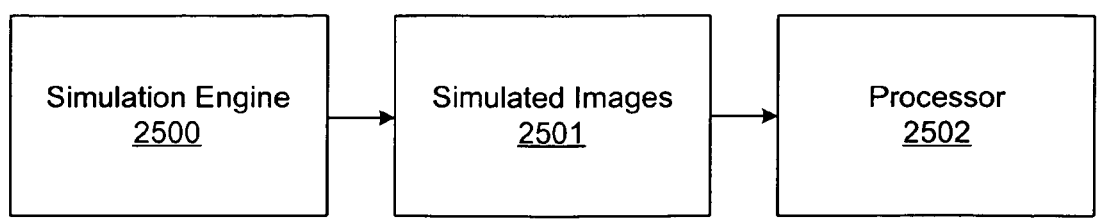
FIG. 25 is a schematic diagram illustrating a block diagram of a different embodiment of a system that is configured to detect defects in a reticle design pattern.

FIG. 25 illustrates another embodiment of a system that is configured to detect defects in a reticle design pattern. As shown in FIG. 25, this system includes simulation engine 2500. Simulation engine 2500 is configured to generate simulated images 2501 of a field in the reticle design pattern. The simulated images illustrate how the field will be printed on a wafer at different values of one or more parameters of a wafer printing process. The field includes a first die and a second die. In addition, the field may include more than two die.

In one example, the simulation engine may be configured to perform vPWQ methods. In particular, the simulation engine may be configured to generate first simulated images that illustrate how the reticle design pattern will be printed on a reticle using a reticle manufacturing process. These first simulated images may be used to generate second simulated images that illustrate how the reticle design pattern printed on the reticle will be printed on a wafer using a wafer printing process. Like the methods described above, these second simulated images may also be generated for different values of one or more parameters of the wafer printing process and may be used as simulated images 2501. The simulation engine may be further configured as described in U.S. patent application Ser. No. 11/048,630 entitled "Computer-Implemented Methods for Detecting Defects in Reticle Design Data" filed Jan. 31, 2005, which is incorporated by reference as if fully set forth herein.

As further shown in FIG. 25, the system includes processor 2502. The processor is coupled to simulation engine 2500. The processor may be coupled to the simulation engine in any manner known in the art such that the processor can receive simulated images 2501 generated by simulation engine 2500. Processor 2502 is configured to detect defects in the field based on a comparison of two or more of the simulated images corresponding to two or more of the different values. The processor may be configured to detect the defects as described further above. In addition, processor 2502 is configured to determine if individual defects located in the first die have substantially the same within die position as individual defects located in the second die. The processor may be configured to perform this determining step as described further above (e.g., by die stacking). The processor may also be configured to perform any other step(s) described herein such as assigning a priority and/or a composite priority to the individual defects. The processor may be further configured as described herein. In addition, the system shown in FIG. 25 may be further configured as described herein.

Program instructions for implementing computer-implemented methods such as those described herein may be transmitted over or stored on a carrier medium. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

The processors described above may take various forms, including a personal computer system, mainframe computer system, workstation, network appliance, Internet appliance, imaging computer, or other device. In general, the term "computer system" may be broadly defined to encompass any device having one or more processors, which executes instructions from a memory medium.

Further modifications and alternative embodiments of various aspects of the invention may be apparent to those skilled in the art in view of this description. For example, two different illumination operating variables (e.g., focus and exposure duration) could be printed on separate halves of a single test wafer to perform different qualifying experiments on the same wafer. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects in a reticle design pattern, comprising:
   acquiring images of a field in the reticle design pattern, wherein the images illustrate how the field will be printed on a wafer at different values of one or more parameters of a wafer printing process, and wherein the field comprises a first die and a second die;
   detecting defects in the field by comparing two or more of the images to each other, wherein the two or more of the images that are compared to each other correspond to two or more of the different values;

determining if individual defects located in the first die have substantially the same within die position as individual defects located in the second die; and assigning a composite priority to the individual defects based on results of said determining in combination with the different values of the one or more parameters of the wafer printing process corresponding to the images of the field in which the individual effects in the first and second die were detected.

2. The method of claim 1, wherein said assigning comprises assigning a higher priority to the individual defects that are located in the first and second die at substantially the same within die position than the individual defects that are not located in the first and second die at substantially the same within die position.

3. The method of claim 1, wherein the substantially the same within die position comprises a range of within die positions defined by a single within die position and a predetermined tolerance for acceptable positional variance.

4. The method of claim 1, wherein said determining comprises determining if the individual defects in the first die having substantially the same within die position as the individual defects located in the second die have one or more different characteristics and determining if the individual defects in the first or second die are random defects obscuring a defect in the reticle design pattern.

5. The method of claim 1, further comprising determining if the individual defects that are located in the first and second die at substantially the same within die position have a characteristic that is substantially the same.

6. The method of claim 5, wherein the characteristic qualifies as being substantially the same if a value of the characteristic is within a range of values for the characteristic, and wherein the range is defined by a single value for the characteristic and a predetermined tolerance for acceptable characteristic variance.

7. The method of claim 1, wherein said assigning comprises assigning a higher priority to the individual defects that are located in the first and second die at substantially the same within die position and have one or more characteristics that are substantially the same than a priority assigned to the individual defects that are located in the first and second die at substantially the same within die position and exhibit differences in the one or more characteristics.

8. The method of claim 1, further comprising selecting the first and second die within the field based on locations of the first and second die within the field.

9. The method of claim 1, wherein the field comprises die for different devices, the method further comprising selecting the first and second die within the field based on the different devices associated with the die.

10. The method of claim 1, wherein a sensitivity of said determining in a first region of the first and second die is different than a sensitivity of said determining in a second region of the first and second die.

11. The method of claim 1, further comprising filtering the individual defects based on results of said determining.

12. The method of claim 1, wherein the images of the field comprise images of the reticle design pattern printed on a wafer using the wafer printing process.

13. The method of claim 1, wherein the images of the field comprise aerial images of the reticle design pattern printed on a reticle.

14. The method of claim 1, wherein the images of the field comprise simulated images.

15. A system configured to detect defects in a reticle design pattern, comprising:

an optical subsystem configured to acquire images of a field in the reticle design pattern, wherein the images illustrate how the field will be printed on a wafer at different values of one or more parameters of a wafer printing process, and wherein the field comprises a first die and a second die; and a processor coupled to the optical subsystem, wherein the processor is configured to:

detect defects in the field by comparing two or more of the images to each other, wherein the two or more of the images that are compared to each other correspond to two or more of the different values;

determine if individual defects located in the first die have substantially the same within die position as individual defects located in the second die; and assign a composite priority to the individual defects based on results of determining if the individual defects located in the first die have substantially the same within die position as the individual defects located in the second die in combination with the different values of the one or more parameters of the wafer printing process corresponding to the images of the field in which the individual defects in the first and second die were detected.

16. The system of claim 15, wherein the optical subsystem is further configured to acquire the images by imaging a wafer on which the reticle design pattern is printed using the wafer printing process.

17. The system of claim 15, wherein the optical subsystem is further configured as an aerial imaging measurement system.

18. The system of claim 17, wherein the aerial imaging measurement system comprises sensors coupled to a substrate and positioned at different heights with respect to a reticle on which the reticle design pattern is formed, and wherein the sensors are configured to acquire the images.

19. A system configured to detect defects in a reticle design pattern, comprising:

a simulation engine configured to generate simulated images of a field in the reticle design pattern, wherein the simulated images illustrate how the field will be printed on a wafer at different values of one or more parameters of a wafer printing process, and wherein the field comprises a first die and a second die; and a processor coupled to the simulation engine, wherein the processor is configured to:

detect defects in the field by comparing two or more of the simulated images to each other, wherein the two or more of the simulated images that are compared to each other correspond to two or more of the different values;

determine if individual defects located in the first die have substantially the same within die position as individual defects located in the second die; and assign a composite priority to the individual defects based on results of determining if the individual defects located in the first die have substantially the same within die position as the individual defects located in the second die in combination with the different values of the one or more parameters of the wafer printing process corresponding to the images of the field in which the individual defects in the first and second die were detected.

* * * * *